United States Patent
Gilad et al.

(10) Patent No.: US 9,078,579 B2
(45) Date of Patent: Jul. 14, 2015

(54) IN VIVO SENSING DEVICE WITH A FLEXIBLE CIRCUIT BOARD

(71) Applicant: GIVEN IMAGING LTD., Yogneam (IL)

(72) Inventors: Zvika Gilad, Haifa (IL); Semion Khait, Tiberias (IL); Chen Mann, Kibbutz Merhavia (IL); Nathan Rubin, Nahariya (IL)

(73) Assignee: GIVEN IMAGING LTD., Yoqneam (IL)

(*) Notice: Subject to any disclaimer, the term of this patent is extended or adjusted under 35 U.S.C. 154(b) by 184 days.

(21) Appl. No.: 13/936,265

(22) Filed: Jul. 8, 2013

(65) Prior Publication Data
US 2013/0296650 A1      Nov. 7, 2013

Related U.S. Application Data

(62) Division of application No. 12/490,711, filed on Jun. 24, 2009, now Pat. No. 8,516,691.

(51) Int. Cl.
*A61B 1/04* (2006.01)
*A61B 5/00* (2006.01)
(Continued)

(52) U.S. Cl.
CPC .............. *A61B 1/041* (2013.01); *A61B 5/6861* (2013.01); *H05K 1/189* (2013.01); *A61B 1/051* (2013.01); *H05K 2201/042* (2013.01); *H05K 2201/10037* (2013.01); *H05K 2201/10121* (2013.01); *H05K 2201/2009* (2013.01); *Y10T 29/49126* (2015.01);
(Continued)

(58) Field of Classification Search
CPC .... A61B 1/041; A61B 1/051; A61B 1/00163; A61B 5/6861; H05K 1/189; H05K 2201/042; H05K 2201/10121; H05K 2201/10106; H05K 2201/10098; Y10T 29/5313; Y10T 29/49133; Y10T 29/49126
USPC .................................................. 600/109, 130
See application file for complete search history.

(56) References Cited

U.S. PATENT DOCUMENTS

| 78,134 A | 5/1858 | Robbins |
|---|---|---|
| 3,509,270 A | 4/1970 | Dube et al. |

(Continued)

FOREIGN PATENT DOCUMENTS

| DE | 3440177 | 5/1986 |
|---|---|---|
| EP | 1104182 | 5/2001 |

(Continued)

OTHER PUBLICATIONS

U.S. Appl. No. 10/213,345, filed Aug. 7, 2002, Glukhovsky.
(Continued)

*Primary Examiner* — John P Leubecker
(74) *Attorney, Agent, or Firm* — Pearl Cohen Zedek Latzer Baratz LLP

(57) ABSTRACT

A flexible circuit board for being inserted into an in-vivo imaging device is provided. The flexible circuit board may include a plurality of flexible installation units connected to one another through flexible connection units. The flexible installation units may be capable of having electrical components disposed thereon at a size suitable for being included in an in-vivo imaging device which may be inserted into a body lumen, e.g., a capsule endoscope. An in-vivo imaging device which may enclose such a full-flexible circuit board is also provided.

17 Claims, 17 Drawing Sheets

(51) Int. Cl.
*H05K 1/18* (2006.01)
*A61B 1/05* (2006.01)

(52) U.S. Cl.
CPC ........ *Y10T 29/49133* (2015.01); *Y10T 29/5313* (2015.01)

(56) References Cited

U.S. PATENT DOCUMENTS

| | | | |
|---|---|---|---|
| 3,529,200 A | 9/1970 | Potter et al. |
| 3,616,532 A | 11/1971 | Beck |
| 3,683,389 A | 8/1972 | Hollis |
| 3,771,516 A | 11/1973 | Corriero |
| 3,791,377 A | 2/1974 | Norby et al. |
| 3,856,000 A | 12/1974 | Chikama |
| 3,971,362 A | 7/1976 | Pope et al. |
| 4,087,960 A | 5/1978 | Koichi |
| 4,178,735 A | 12/1979 | Jackson |
| 4,239,040 A | 12/1980 | Hosoya et al. |
| 4,262,632 A | 4/1981 | Hanton et al. |
| 4,278,077 A | 7/1981 | Mizumoto |
| 4,319,563 A | 3/1982 | Kubota |
| 4,439,197 A | 3/1984 | Honda et al. |
| 4,447,677 A | 5/1984 | Miyahra et al. |
| 4,628,150 A | 12/1986 | Luc |
| 4,646,724 A | 3/1987 | Sato et al. |
| 4,668,884 A | 5/1987 | Amao et al. |
| 4,689,621 A | 8/1987 | Kleinberg |
| 4,741,327 A | 5/1988 | Yabe |
| 4,742,183 A | 5/1988 | Soloway et al. |
| 4,742,817 A | 5/1988 | Kawashima et al. |
| 4,803,992 A | 2/1989 | Lemelson |
| 4,807,598 A | 2/1989 | Hasegawa |
| 4,812,726 A | 3/1989 | Benii et al. |
| 4,819,620 A | 4/1989 | Okutsu |
| 4,844,076 A | 7/1989 | Lesho et al. |
| 4,860,732 A | 8/1989 | Hasegawa et al. |
| 4,936,823 A | 6/1990 | Colvin et al. |
| 4,939,792 A | 7/1990 | Urbish et al. |
| 4,940,997 A | 7/1990 | Hamlin et al. |
| 5,021,888 A | 6/1991 | Kondou et al. |
| 5,025,704 A | 6/1991 | Davis |
| 5,042,486 A | 8/1991 | Pfeiler et al. |
| 5,081,041 A | 1/1992 | Yafuso et al. |
| 5,109,870 A | 5/1992 | Silny et al. |
| 5,181,065 A * | 1/1993 | Hara ............................ 396/542 |
| 5,187,572 A | 2/1993 | Nakamura et al. |
| 5,211,165 A | 5/1993 | Dumoulin et al. |
| 5,220,198 A | 6/1993 | Tsuji |
| 5,241,170 A | 8/1993 | Field, Jr. et al. |
| 5,250,371 A | 10/1993 | Kleinert, III et al. |
| 5,267,033 A | 11/1993 | Hoshino |
| 5,279,607 A | 1/1994 | Schentag et al. |
| 5,318,024 A | 6/1994 | Kittrell et al. |
| 5,330,427 A | 7/1994 | Weissenburger |
| 5,368,027 A | 11/1994 | Lubbers et al. |
| 5,381,784 A | 1/1995 | Adair |
| 5,395,366 A | 3/1995 | D'Andrea et al. |
| 5,398,670 A | 3/1995 | Ortiz et al. |
| 5,398,689 A | 3/1995 | Conner et al. |
| 5,415,181 A | 5/1995 | Hogrefe et al. |
| 5,426,263 A | 6/1995 | Potter et al. |
| 5,429,132 A | 7/1995 | Guy et al. |
| 5,434,362 A | 7/1995 | Klosowiak et al. |
| 5,448,511 A | 9/1995 | Paurus et al. |
| 5,454,366 A | 10/1995 | Ito et al. |
| 5,472,804 A | 12/1995 | Austin et al. |
| 5,479,935 A | 1/1996 | Essen-Moller |
| 5,495,114 A | 2/1996 | Adair |
| 5,508,781 A | 4/1996 | Imai et al. |
| 5,549,109 A | 8/1996 | Samson et al. |
| 5,558,640 A | 9/1996 | Pfeiler et al. |
| 5,604,531 A | 2/1997 | Iddan et al. |
| 5,679,216 A | 10/1997 | Takayama et al. |
| 5,681,260 A | 10/1997 | Ueda |
| 5,697,384 A | 12/1997 | Miyawaki et al. |
| 5,725,474 A | 3/1998 | Yasui et al. |
| 5,734,418 A | 3/1998 | Danna |
| 5,754,313 A | 5/1998 | Pelchy et al. |
| 5,800,350 A | 9/1998 | Coppelson et al. |
| 5,807,266 A | 9/1998 | Itonaga et al. |
| 5,812,187 A | 9/1998 | Watanabe |
| 5,817,015 A | 10/1998 | Adair |
| 5,819,736 A | 10/1998 | Avny et al. |
| 5,833,603 A | 11/1998 | Kovacs et al. |
| 5,837,196 A | 11/1998 | Pinker et al. |
| 5,857,963 A | 1/1999 | Pelchy et al. |
| 5,908,294 A | 6/1999 | Schick et al. |
| 5,913,820 A | 6/1999 | Bladen et al. |
| 5,929,901 A | 7/1999 | Adair et al. |
| 5,984,875 A | 11/1999 | Brune |
| 5,986,693 A | 11/1999 | Adair et al. |
| 5,993,378 A | 11/1999 | Lemelson |
| 6,043,839 A | 3/2000 | Adair et al. |
| 6,069,991 A | 5/2000 | Hibbs-Brenner et al. |
| 6,088,606 A | 7/2000 | Ignotz et al. |
| 6,099,482 A | 8/2000 | Brune et al. |
| 6,121,922 A | 9/2000 | Mohan |
| 6,149,581 A | 11/2000 | Klingenstein |
| 6,174,291 B1 | 1/2001 | McMahon |
| 6,228,048 B1 | 5/2001 | Robbins |
| 6,233,476 B1 | 5/2001 | Stommer et al. |
| 6,240,312 B1 | 5/2001 | Alfano et al. |
| 6,273,904 B1 | 8/2001 | Chen et al. |
| 6,285,897 B1 | 9/2001 | Kilcoyne et al. |
| 6,313,456 B1 | 11/2001 | Miyashita et al. |
| 6,324,418 B1 | 11/2001 | Crowley et al. |
| 6,338,347 B1 | 1/2002 | Chung |
| 6,366,186 B1 | 4/2002 | Hill et al. |
| 6,369,812 B1 | 4/2002 | Lyriboz et al. |
| 6,371,927 B1 | 4/2002 | Brune et al. |
| 6,395,562 B1 | 5/2002 | Hammock et al. |
| 6,400,338 B1 | 6/2002 | Mejia et al. |
| 6,417,885 B1 | 7/2002 | Suzuki et al. |
| 6,449,006 B1 | 9/2002 | Shipp |
| 6,475,145 B1 | 11/2002 | Baylor |
| 6,488,694 B1 | 12/2002 | Lau et al. |
| 6,547,721 B1 | 4/2003 | Higuma et al. |
| 6,547,723 B1 | 4/2003 | Ouchi |
| 6,584,348 B2 | 6/2003 | Glukhovsky |
| 6,607,301 B1 | 8/2003 | Glukhovsky et al. |
| 6,632,175 B1 | 10/2003 | Marshall |
| 6,692,430 B2 | 2/2004 | Adler |
| 6,709,387 B1 | 3/2004 | Glukhovsky et al. |
| 6,800,060 B2 | 10/2004 | Marshall |
| 6,836,377 B1 | 12/2004 | Kislev et al. |
| 6,887,196 B2 | 5/2005 | Arai et al. |
| 6,904,308 B2 | 6/2005 | Frisch et al. |
| 6,934,573 B1 | 8/2005 | Glukhovsky et al. |
| 6,939,292 B2 | 9/2005 | Mizuno |
| 6,944,031 B2 | 9/2005 | Takami |
| 6,950,690 B1 | 9/2005 | Meron et al. |
| 6,958,035 B2 | 10/2005 | Friedman et al. |
| 7,009,634 B2 | 3/2006 | Iddan et al. |
| 7,039,453 B2 | 5/2006 | Mullick et al. |
| 7,118,529 B2 | 10/2006 | Glukhovsky et al. |
| 7,119,814 B2 | 10/2006 | Meron et al. |
| 7,192,397 B2 | 3/2007 | Lewkowicz et al. |
| 7,468,044 B2 | 12/2008 | Iddan |
| 7,616,238 B2 | 11/2009 | Avni et al. |
| 7,727,169 B1 | 6/2010 | Lewkowicz et al. |
| 7,877,134 B2 | 1/2011 | Glukhovsky |
| 7,931,584 B2 | 4/2011 | Akagi et al. |
| 7,998,065 B2 | 8/2011 | Avni |
| 2001/0006252 A1 | 7/2001 | Kim et al. |
| 2001/0017649 A1 | 8/2001 | Yaron |
| 2001/0025135 A1 | 9/2001 | Naito et al. |
| 2001/0035902 A1 | 11/2001 | Iddan et al. |
| 2001/0051766 A1 | 12/2001 | Gazdinski |
| 2002/0015952 A1 | 2/2002 | Anderson et al. |
| 2002/0080233 A1* | 6/2002 | Irion et al. ............... 348/65 |
| 2002/0095187 A1 | 7/2002 | Thompson et al. |
| 2002/0103417 A1 | 8/2002 | Gazdzinski |
| 2002/0109774 A1 | 8/2002 | Meron et al. |

(56) References Cited

U.S. PATENT DOCUMENTS

| | | |
|---|---|---|
| 2002/0143239 A1 | 10/2002 | Henzler |
| 2002/0146368 A1 | 10/2002 | Meron et al. |
| 2002/0158976 A1 | 10/2002 | Vne et al. |
| 2002/0171669 A1 | 11/2002 | Meron et al. |
| 2002/0173718 A1 | 11/2002 | Frisch et al. |
| 2002/0177779 A1 | 11/2002 | Adler et al. |
| 2002/0193664 A1 | 12/2002 | Ross et al. |
| 2002/0198439 A1 | 12/2002 | Mizuno |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0032863 A1 | 2/2003 | Kazakevich |
| 2003/0043263 A1 | 3/2003 | Glukhovsky et al. |
| 2003/0045790 A1 | 3/2003 | Lewkowics et al. |
| 2003/0073935 A1 | 4/2003 | Segawa et al. |
| 2003/0077223 A1 | 4/2003 | Glukhovsky et al. |
| 2003/0114742 A1 | 6/2003 | Lewkowicz |
| 2003/0117491 A1 | 6/2003 | Avni et al. |
| 2003/0130562 A1 | 7/2003 | Barbato et al. |
| 2003/0151661 A1 | 8/2003 | Davidson et al. |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0195415 A1 | 10/2003 | Iddan |
| 2003/0208107 A1 | 11/2003 | Refael |
| 2003/0214579 A1 | 11/2003 | Iddan |
| 2003/0214580 A1 | 11/2003 | Iddan |
| 2003/0216622 A1 | 11/2003 | Meron et al. |
| 2004/0021792 A1* | 2/2004 | Yasui ............................ 348/373 |
| 2004/0027459 A1 | 2/2004 | Segawa et al. |
| 2004/0027500 A1 | 2/2004 | Davidson et al. |
| 2004/0087832 A1 | 5/2004 | Glukhovsky et al. |
| 2004/0106849 A1 | 6/2004 | Cho et al. |
| 2004/0138532 A1 | 7/2004 | Glukhovsky |
| 2004/0171914 A1 | 9/2004 | Avni |
| 2004/0215059 A1 | 10/2004 | Homan et al. |
| 2004/0225189 A1 | 11/2004 | Kimoto et al. |
| 2004/0225190 A1 | 11/2004 | Kimoto et al. |
| 2004/0254455 A1 | 12/2004 | Iddan |
| 2004/0258328 A1 | 12/2004 | Adler |
| 2005/0043583 A1 | 2/2005 | Killmann et al. |
| 2005/0043586 A1 | 2/2005 | Suzushima |
| 2005/0049461 A1 | 3/2005 | Honda et al. |
| 2005/0068416 A1 | 3/2005 | Glukhovsky et al. |
| 2005/0080342 A1 | 4/2005 | Gilreath et al. |
| 2005/0124858 A1 | 6/2005 | Matsuzawa et al. |
| 2005/0171398 A1 | 8/2005 | Khait et al. |
| 2005/0259487 A1 | 11/2005 | Glukhovsky et al. |
| 2005/0270169 A1 | 12/2005 | Drader |
| 2006/0004255 A1 | 1/2006 | Iddan et al. |
| 2006/0004256 A1 | 1/2006 | Gilad et al. |
| 2006/0004257 A1 | 1/2006 | Gilad et al. |
| 2006/0004276 A1* | 1/2006 | Iddan et al. ................... 600/407 |
| 2006/0015013 A1 | 1/2006 | Gilad et al. |
| 2006/0020171 A1 | 1/2006 | Gilreath |
| 2006/0069310 A1 | 3/2006 | Couvillon |
| 2006/0100496 A1 | 5/2006 | Avron |
| 2006/0104057 A1 | 5/2006 | Avron et al. |
| 2006/0241407 A1 | 10/2006 | Scarantino et al. |
| 2006/0241422 A1 | 10/2006 | Muratayev et al. |
| 2006/0264709 A1 | 11/2006 | Fujimori et al. |
| 2007/0118012 A1 | 5/2007 | Gilad |
| 2007/0229656 A1 | 10/2007 | Khait et al. |
| 2008/0021281 A1 | 1/2008 | Fujimori |
| 2008/0081949 A1* | 4/2008 | Gilad ............................ 600/160 |
| 2010/0174141 A1* | 7/2010 | Gilad et al. .................... 600/118 |

FOREIGN PATENT DOCUMENTS

| | | |
|---|---|---|
| FR | 2362556 | 8/1976 |
| FR | 2688997 | 10/1993 |
| GB | 2339922 | 9/2000 |
| JP | 63-262613 | 10/1988 |
| JP | 3289779 | 12/1991 |
| JP | 4109927 | 4/1992 |
| JP | 1992-144533 | 5/1992 |
| JP | 4144533 | 5/1992 |
| JP | 4180736 | 6/1992 |
| JP | 5015515 | 1/1993 |
| JP | 6114037 | 4/1994 |
| JP | 06-138400 | 5/1994 |
| JP | 6285044 | 10/1994 |
| JP | 71-11985 | 5/1995 |
| JP | 7289504 | 11/1995 |
| JP | 2000342522 | 12/2000 |
| JP | 2000342524 | 12/2000 |
| JP | 2000342525 | 12/2000 |
| JP | 2001-095755 | 4/2001 |
| JP | 2001-095756 | 4/2001 |
| JP | 2001-104241 | 4/2001 |
| JP | 2001-104242 | 4/2001 |
| JP | 2001-104243 | 4/2001 |
| JP | 2001-104244 | 4/2001 |
| JP | 2001-104287 | 4/2001 |
| JP | 2001-112710 | 4/2001 |
| JP | 2001091860 | 4/2001 |
| JP | 2001112709 | 4/2001 |
| JP | 2001112740 | 4/2001 |
| JP | 2001-13718 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2003-210394 | 7/2003 |
| JP | 2005-111142 | 4/2005 |
| JP | 2005-204802 | 8/2005 |
| WO | WO 92-21307 | 12/1992 |
| WO | WO 98/11816 | 3/1998 |
| WO | WO 99/32028 | 7/1999 |
| WO | WO 01/08548 | 2/2001 |
| WO | WO 01/50941 | 7/2001 |
| WO | WO 02-067593 | 8/2002 |

OTHER PUBLICATIONS

E. N. Rowlands, H. S. Wolff "The Radio Pill" British Commmunicaitons and Electronics, pp. 598-601, Aug. 1960.

Rex Caum "Wellesley company sends body monitors into space"—Crum, Apr. 24-30, 1998.

Swain CP, Gong F, Mills TN. "Wireless transmission of a color television moving image from the stomach using a miniature CCD camera, light source and microwave transmitter" Gut;39:A26. Apr. 1997.

BBC News Online—Pill camera to broadcast from the gut, ,www.news.bbc.co.uk, Feb. 21, 2000.

Gavriel D. Meron: "The Development of the Swallowable Video Capsule (M2A)" Gastrointestinal Endoscopy, vol. 52, No. 6, Dec. 2000, pp. 817-819.

Appleyard et al. "A Randomized Trial Comparing Wireless Capsule Endoscopy With Push Enteroscopy for the Detection of Small—Bowel Lesions" Gastroenterology, vol. 119, No. 6, Dec. 2000 (2000-12), pp. 1431-1438.

Shin-Ichi, et al.: "Robots for the Future", Nov. 29, 2001.

"Video Camera to TAKE", RF System Lab, Dec. 25, 2001.

Wang, et al.: "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

www.rfnorika.com-NORIKA3, The Robotic Capsule for Diagnosis and Treatment inside a Patient, Jan 1, 2002.

R. Stuart Mackay "Bio-Medical Telemetry: Sensing and Transmitting Biological Information from Animals and Man" John Wiley and Sons, New York, pp. 244-245 , 1970.

S. G. Demos, H. B. Radousky, and R. R. Alfano "Deep Subsurface Imaging in Tissues Using Spectral and Polarization Filtering" vol. 7, No. 1 Optics Express, pp. 23-28, Jul. 3, 2000.

Yarbrough, III et al. "Evaluation of the Heidelberg pH Capsule: Method of Tubeless Gastric Analysis" The American Journal of Surgery, vol. 117, pp. 185-192, Feb. 1969.

(56) References Cited

OTHER PUBLICATIONS

Lange et al. "Heidelberger Kapsel—ein Kleinstsender fur die pH-Messung im Magen", Telefunken-Zeitung, Jg 36, Heft 5, pp. 265-270, 1963.
Craford et al. "In Pursuit of the Ultimate Lamp", Scientific American, Feb. 2001.
"Manual of Photogrammetry", Thompson (Ed.), Third Edition, vol. Two, by the American Society of Photogrammetry Manual of Photogrammetry Copyright 1944, 1952, 1966.
www.jason.net/tinycam.htm,Tiny Cam © 2001, printed Dec. 19, 2001.
www.middleeasthealthmag.com/article2.htm—Review proves the value of computers, © 2001, printed 29 Nov. 2001.
www.pedinc.com Personal electronic devices, © 1997.
"New Smart Plastic has Good Memory"—Turke, European Medical Device Manufacturer, devicelink.com.
"The Heidelburg pH Capsule System Telemetric Fasting Gastric Analysis", Heidelburg International. Incorporated.
Joseph Fjelstad, Flexible Ciruit Technology, $3^{rd}$ Edition, Sep. 2006, BR Publishing Inc, USA, ISBN 0-9667-075-0-8.
John Dzarnoski, 3D Chip Packaging for Class I Medical Devices, Starkey Laboratories, Oct. 16, 2008.
International Search Report and Written Opinion, issued Oct. 27, 2010, for PCT Internation Application No. PCT/IL10/00482.

* cited by examiner

IN VIVO SENSING DEVICE WITH A FLEXIBLE CIRCUIT BOARD

CROSS REFERENCE TO RELATED APPLICATIONS

This application claims the benefit of U.S. patent application Ser. No. 12/490,711, filed on Jun. 24, 2009, now U.S. Pat. No. 8,516,691, published as US Patent Application Publication No. 2010/0326703 and entitled METHOD OF ASSEMBLY OF AN IN VIVO IMAGING DEVICE WITH A FLEXIBLE CIRCUIT BOARD, which is incorporated by reference in its entirety herein.

FIELD OF THE INVENTION

The present invention relates to an in-vivo imaging device such as a capsule endoscopy and method of assembly thereof.

BACKGROUND OF THE INVENTION

In vivo imaging may include the use of an in vivo imager from which image data may be transmitted to an external receiving system. For example, an ingestible capsule, which may be swallowed by a patient, may include an image sensor for imaging the gastrointestinal (GI) tract and a transmitter for transmitting the image data. In some ingestible capsules, the electronic components within the capsule may be arranged on several printed circuit boards, each printed circuit board containing different components of the capsule. For example, the image sensor, typically a silicon chip, may be positioned on one printed circuit board, whereas the transmitter may be positioned on a separate printed circuit board (PCB).

In some cases, the printed circuit boards are aligned along an axis of the in-vivo sensing device, e.g., a capsule, and are electrically connected by a plurality of wires. However, assembly of in-vivo sensing devices having several boards connected by wires, which takes into account the cooperation between the electrical and electronic components and the required optical properties of the in-vivo sensing device, may be complex and may hinder, for example, large scale production.

Some swallowable capsules may include more than one imaging assembly, each including an imager, illumination sources, and an optical assembly, so that the gastrointestinal (GI) tract may be viewed from more than one direction or angle. Acquiring images of the GI tract from various directions or angles allows for collection of more information on the condition of the GI tract, such that a better assessment of the patient's physical condition may be made. However, more than one imaging assembly may lead to there being more electronic components within the limited internal space of the capsule and to a more complex arrangement of the electronic components within the capsule, which may hinder large scale production more than with one imaging assembly.

SUMMARY OF THE INVENTION

Embodiments of the present invention provide an in-vivo sensing device with a flexible circuit board and method for easy and simple assembly of the flexible circuit board in the in-vivo sensing device.

Methods of assembly of an in-vivo device with two imagers are described in U.S. patent application Ser. No. 11/603,123, entitled "Method of Assembling an In-vivo Imaging Device", filed on Nov. 22, 2006 published on May 24, 2007 as United States Patent Application Publication Number 2007/0118012. This application describes a method of folding a rigid-flex PCB comprising two optical heads into an in-vivo device's housing. However, the present invention provides a different design of a dual imaging assembly circuit board and an easy method of assembly of such a circuit board.

In some embodiments of the present invention, an in-vivo sensing device may include a flexible circuit board. In some embodiments, the flexible circuit board may be a full-flex printed circuit board (full-flex PCB), i.e., the PCB includes flexible installation units (capable of having electrical components disposed thereon) attached to one another through flexible connection units. According to some embodiments, when the full-flex PCB is in an unfolded configuration, all the electrical and electronic components are mounted on the same side of the board. Full flex PCBs are available from a number of manufacturers, such as, ELTEK, Printed Circuits, HIGHTEC and Dyconex.

A full-flex PCB which includes a one-side assembly configuration, i.e., in which the electronic components are mounted on only one side of the installation units, is easier to design and assemble than a rigid-flex PCB, which includes a two-sided assembly configuration, i.e., in which the electronic components are mounted on both sides of the rigid portions. For example, a one-side assembly full-flex PCB is easier to handle since care need be taken with only one side of the PCB instead of with both. Thus, there is less limitation in the topographical arrangement of the various electrical components, unlike when arranging components on both sides of a rigid portion. In a full-flex PCB, each component may be mounted on a different "branch" of a flexible installation unit and all components are positioned onto the same side of the full-flex PCB. In some embodiments, it may also be possible to conduct various tests during assembly, such as electricity tests and optical tests, when the full-flex PCB is in its unfolded configuration, rather than having to wait until the PCB is installed within a capsule before conducting such tests.

A full-flex PCB has almost no limit in "bending radius", unlike some rigid-flex PCB where the connections between the rigid portions and the flexible portions are limited in the folding radius e.g., when the PCB is constrained to fit inside a swallowable in-vivo device. In some rigid-flex PCB, the folding radius may be limited to approximately 1 mm while in a full-flex PCB there is substantially no limit.

In some embodiments, due to the vagaries of mass production, the rigid portion of the rigid-flex PCB may have a thickness that differs slightly from the exact size as designed, since the tolerance during production is quite high. During mass production, the rigid portion of the PCB may be designed to have a final thickness of typically between 0.5 mm and 0.8 mm but may also have a tolerance of about ±0.1 mm, which is of the same order of magnitude as the final thickness. Such a high tolerance may lead to a large variance in the thickness of the rigid portion. However, a full-flex PCB has a final thickness of typically 0.05-0.06 mm, and the tolerance is of about ±5 µm (or 0.005 mm) which is of an order of magnitude smaller than the final thickness of the full-flex PCB. Such a tight tolerance in the "z" axis, as the full-flex PCB has, is crucial when assembling optical systems. Furthermore, a full-flex PCB has a tight tolerance in the "x-y" axes as well due to a very accurate layout cutting of the PCB. The tight tolerances described may assist in adjusting the illumination sources in an accurate position along the folded full-flex PCB, e.g., the orientation in space in "x-y" axes of the LED ring around the lens holder. The accurate layout cutting of the PCB ensures that the LED ring surrounds the lens holder while conforming to a specific optical layout. Further, the full-flex PCB's tight tolerances may assist in adjusting the position of the entire imaging assembly (which may include the illumination sources, the imager and the optical assembly) in relation to the optical window (in "x-y-z" axes), so as to avoid incidence of stray light from the optical window that covers the imaging assembly.

Another advantage of the full-flex PCB may be the ability of the optical window or dome to be locked onto the imaging assembly before the imaging assembly is locked within the device's housing. This ensures that the imaging assembly is well-positioned in relation to the dome in order to avoid misalignment of the optical components, only after which is the imaging assembly and the dome locked inside the device's housing. For example, this feature may be important during assembly of an in-vivo device with more than one imaging assembly, e.g., two imaging assemblies.

In some embodiments, the full-flex PCB may include a long flexible connection unit that may connect one imaging assembly to the other. When the long flexible connection unit is longer than the length of the device's housing, the two optical windows are able to be locked over the respective imaging assemblies, and only then may the power source be inserted and may the optical windows be attached to the device's housing to form a closed housing. Even though the long flexible connection unit is longer than the length of the device's housing, its small thickness allows the extra length of PCB to be pushed inside the device's housing and the optical windows at both ends of the housing to be closed without causing any damage to the long flexible connection unit.

A full-flex PCB also has lighter weight than a rigid-flex PCB has. This may be an important feature when the full-flex PCB is intended to be part of a device that needs to have a specific weight. For example, a swallowable capsule that is intended to acquire images of the colon should have specific gravity (SG) of around 1, such that the capsule may be able to float while being partially submerged in the in-vivo fluids, as a capsule with SG ~1 is known to achieve an easier and faster passage through the colon, specifically in the cecum area, where content tends to submerge. Use of a full-flex PCB may assist in keeping a low capsule weight, which may then be adjusted to have SG ~1, by adding weight through other components, for example, by thickening plastic parts which form the capsule's housing.

For these reasons and others, the full-flex design disclosed in the present invention may be a useful design to be incorporated in an in-vivo sensing device.

BRIEF DESCRIPTION OF THE DRAWINGS

The present invention will be understood and appreciated more fully from the following detailed description taken in conjunction with the appended drawings in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

It is noted that some embodiments of the present invention may be directed to an autonomous, typically ingestible in-vivo device. Other embodiments need not be ingestible. Devices or systems according to embodiments of the present invention may be similar to embodiments described in U.S. Pat. No. 7,009,634 and/or United States Patent Application Publication No. 2007/0118012, each of which is assigned to the common assignee of the present invention and each of which is hereby fully incorporated by reference, and to the PillCam® Colon capsule endoscopes of the common assignee of the present invention. Furthermore, a receiving and/or display system suitable for use with embodiments of the present invention may also be similar to embodiments described in U.S. Pat. No. 6,904,308 and/or U.S. Pat. No. 7,119,814, each of which is assigned to the common assignee of the present invention and each of which is hereby fully incorporated by reference, and to the RAPID® Software and Workstation of the common assignee of the present invention. Devices and systems as described herein may also have other configurations and other sets of components.

Figure 1:
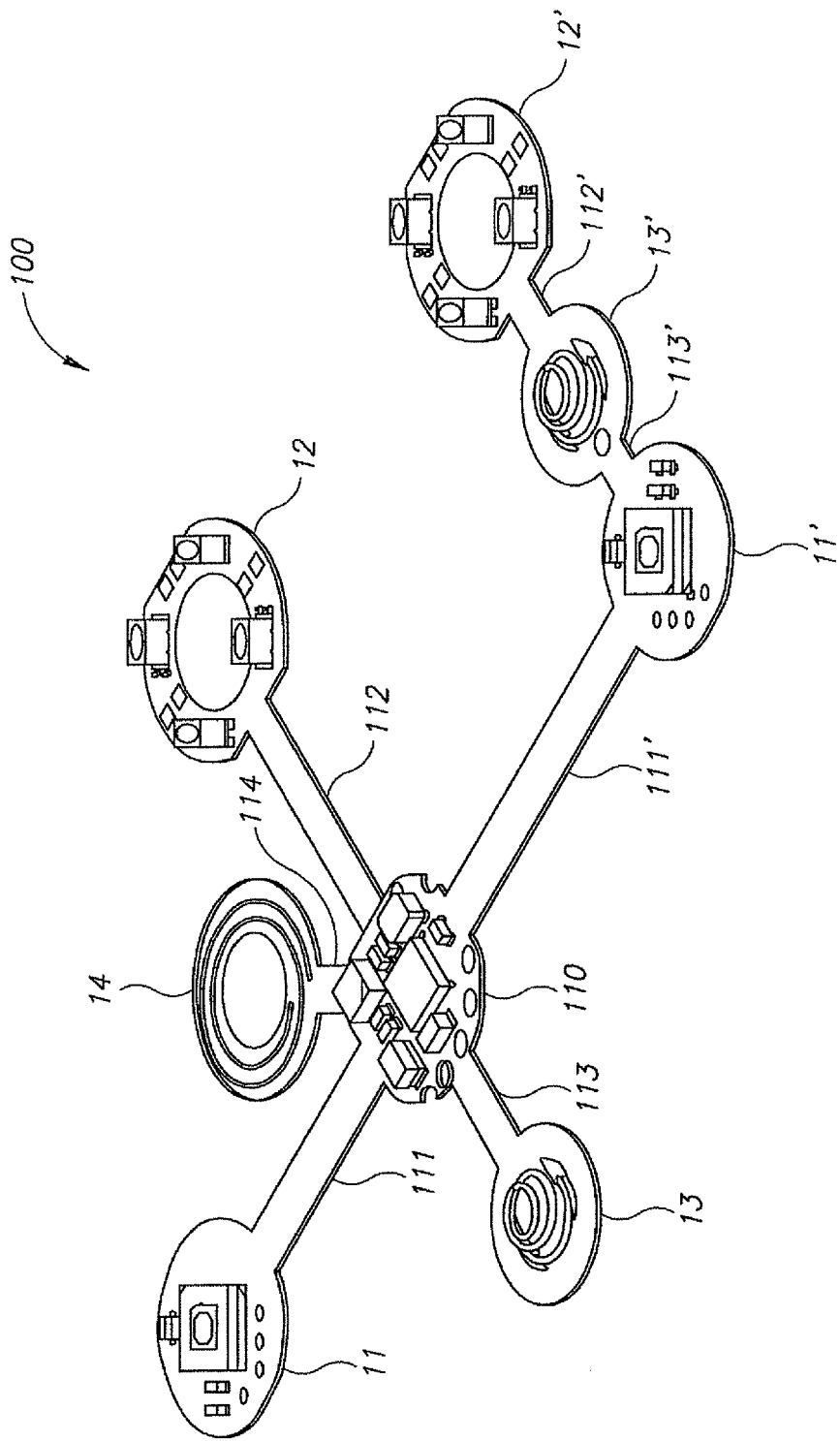
FIG. 1 is a schematic illustration of a top view of a full-flex PCB in an unfolded configuration, in accordance with an embodiment of the present invention.

Reference is now made to FIG. 1, which shows a schematic illustration of a top perspective view of a full-flex PCB 100 in an unfolded configuration, in accordance with an embodiment of the present invention. According to some embodiments, full-flex PCB 100 in its folded configuration may be inserted into a capsule with two optical domes, as described in U.S. Patent Application Publication No. 2002/0109774, to Meron et al., which is assigned to the common assignee of the present invention and which is hereby fully incorporated by reference.

According to some embodiments, full-flex PCB 100 may comprise a plurality of flexible installation units which may be connected to each other through flexible connection units. A flexible connection unit typically connects between two flexible installation units. In some embodiments, full-flex PCB 100 may comprise two sides; one side is configured to have electrical components installed onto it (onto the flexible installation units), while the other side is free of components.

According to some embodiments, full-flex PCB 100 may be designed to be encapsulated so as to operate in an in-vivo autonomous sensing device. When in an encapsulated configuration, either in a shape of a sphere, an elongated capsule or any other shape suitable for being inserted into a patient, the in-vivo sensing device may sense a condition of the in-vivo environment, e.g., acquire images of a lumen it passes through. In some embodiments, the in-vivo sensing device within which full-flex PCB 100 is encapsulated may be a swallowable or ingestible device that may travel through a body lumen, sensing as it moves along. In some embodiments, the in-vivo sensing device may comprise an imager in order to acquire images of a body lumen or cavity, for example, the gastrointestinal (GI) tract.

According to some embodiments, the in-vivo sensing device may further transmit the sensed data (e.g., the acquired images) to an external receiver and/or display system, in order for a physician or other specialist to be able to view the sensed data and give his diagnosis evaluating the patient's condition.

According to some embodiments of the present invention, full-flex PCB 100 may comprise a flexible installation unit 110 capable of having a transmitter disposed thereon. According to some embodiments of the present invention, the flexible installation unit 110 may include a transmitter/receiver for transmitting and/or receiving image and other (e.g., non-image) information to a receiving device. The transmitter/receiver may be an ultra low power radio frequency (RF) transmitter, possibly provided in chip scale packaging, and may be combined with a controller or any analog or digital circuit. The transmitter/receiver may transmit and/or receive via, for example, an embedded antenna installed on flexible installation unit 14. Other methods of transmission may be used. In some embodiments, flexible installation unit 110 may comprise an ASIC which may also act as a controller and include circuitry and functionality for controlling the in-vivo sensing device, although a separate control unit may be used. The ASIC may further include a processor for performing initial processing of the sensed data (e.g. in-vivo images) before transmitting the data to an external receiver or display system.

In some embodiments, flexible installation unit 110 capable of receiving a transmitter may be connected through flexible connection unit 111' to flexible installation unit 11' capable of having a first imager disposed thereon and through flexible connection unit 111 to flexible installation unit 11 capable of having a second imager disposed thereon. The imager installed on each of the flexible installation units 11 and 11' may be a complementary metal oxide semiconductor (CMOS) imaging camera. The CMOS imager is typically an ultra low power imager and is provided in chip scale packaging (CSP). Other types of CMOS imagers may be used. In another embodiment, another imager may be used, such as a CCD imager, or another imager. According to other embodiments, a 256×256 or a 320×320 pixel imager may be used. Pixel size may be between 5 to 6 microns. According to some embodiments, pixels may be each fitted with a micro lens. Other dimensions for imagers and/or other numbers of pixels may be used.

According to some embodiments, flexible installation unit 11' capable of having a first imager disposed thereon may be connected through flexible connection unit 113' to a flexible installation unit 13' capable of having a first battery contact disposed thereon. In some embodiments, flexible installation unit 110 may further be connected through flexible connection unit 113 to a flexible installation unit 13 capable of having a second battery contact disposed thereon. According to some embodiments, the battery contacts installed onto flexible installation units 13 and 13' may be a coiled spring (as shown in FIG. 1), a pogo pin (as the "Pogo" pin commercially available from Everett Charles Technologies), a flat tab that presses against the battery or any other battery contact of the sort. In some embodiments, the batteries that would be in contact with the battery contacts, after the full-flex PCB 100 is folded, so as to provide power to all the electrical components installed on the full-flex PCB 100, may include silver oxide batteries, lithium batteries, or other electrochemical cells having a high energy density, or the like. Other power sources may be used. For example, the full-flex PCB 100 may include a power source other than batteries. Such a power source may be capable of harvesting power from an external power source and providing it to the in-vivo sensing device.

In some embodiments, flexible installation unit 110 capable of having a transmitter mounted thereon is connected through flexible connection unit 112 to a flexible installation unit 12 capable of having at least one illumination source disposed thereon, and flexible installation unit 11' capable of having a first imager disposed thereon may be connected through flexible connection unit 112' to a flexible installation unit 12' capable of receiving at least one illumination source. In some embodiments, the flexible connection unit 112' may directly connect between flexible installation unit 13' capable of having a first battery contact mounted thereon and flexible installation unit 12' capable of having an illumination source mounted thereon. According to some embodiments, the illumination source installed on full-flex PCB 100 may be, for example, a set of light emitting diodes (LEDs), organic LEDs (OLEDs), vertical-cavity surface-emitting laser (VCSEL) or other suitable light sources for providing light to illuminate objects in-vivo.

According to some embodiments, the illumination source installed on flexible installation unit 12 may be of a different kind than that installed on flexible installation unit 12'. In some embodiments, the flexible installation units 12 and 12' may include illumination sources which illuminate in different spectra. For example, illumination source installed on flexible installation unit 12 may be white light, while the illumination source installed on flexible installation unit 12' may be of a narrower spectrum, e.g., blue. Blue spectrum is known to penetrate the tissue, unlike white light, and so may aid in acquiring additional information on tissue characteristics, e.g., a "blue" image may show blood vessels beneath the tissue surface, which would not have been shown in white light illumination.

In some embodiments, flexible installation unit 110 may further be connected through flexible connection unit 114 to flexible installation unit 14 capable of having an antenna disposed thereon. In some embodiments, the antenna installed on flexible installation unit 14 may be embedded within flexible installation unit 14. An antenna embedded within flexible installation unit 14 may be similar to embodiments described in U.S. Patent Application Publication No. 2006/0241422, which is assigned to the common assignee of the present invention and which is hereby fully incorporated by reference. In other embodiments, the antenna need not be embedded and may comprise a coiled spring, for example.

In some embodiments, other or additional flexible installation units may be connected to flexible installation unit 110 through an additional branch, i.e., through an additional flexible connection unit. Examples of sensors capable of being installed on the additional flexible installation units may be: pH sensors, temperature sensors, electric impedance sensors for measuring the impedance of in-vivo tissue, chemical or biological chambers for performing a chemical or biological analysis of a condition in-vivo, etc.

In other embodiments, full-flex PCB 100 may be configured to be inserted into a capsule with only one imaging assembly and one optical window. For example, flexible installation unit 110 capable of having a transmitter disposed thereon may be connected through flexible connection unit 111 to flexible installation unit 11 capable of having an imager disposed thereon, and through flexible connection unit 114 it may further be connected to flexible installation unit 14 capable of having an antenna disposed thereon. Flexible installation unit 110 may further be connected through flexible connection unit 112 to a flexible installation unit 12 capable of having illumination sources disposed thereon. Flexible installation unit 110 may be connected through flexible connection unit 111' to flexible installation unit 13' capable of having a first battery contact disposed thereon and through flexible connection unit 113 to flexible installation unit 13 capable of having a second battery contact disposed thereon. In this embodiment, full-flex PCB 100 does not include flexible installation units capable of having a second imager disposed thereon and a second illumination source, as described above.

Figure 2:
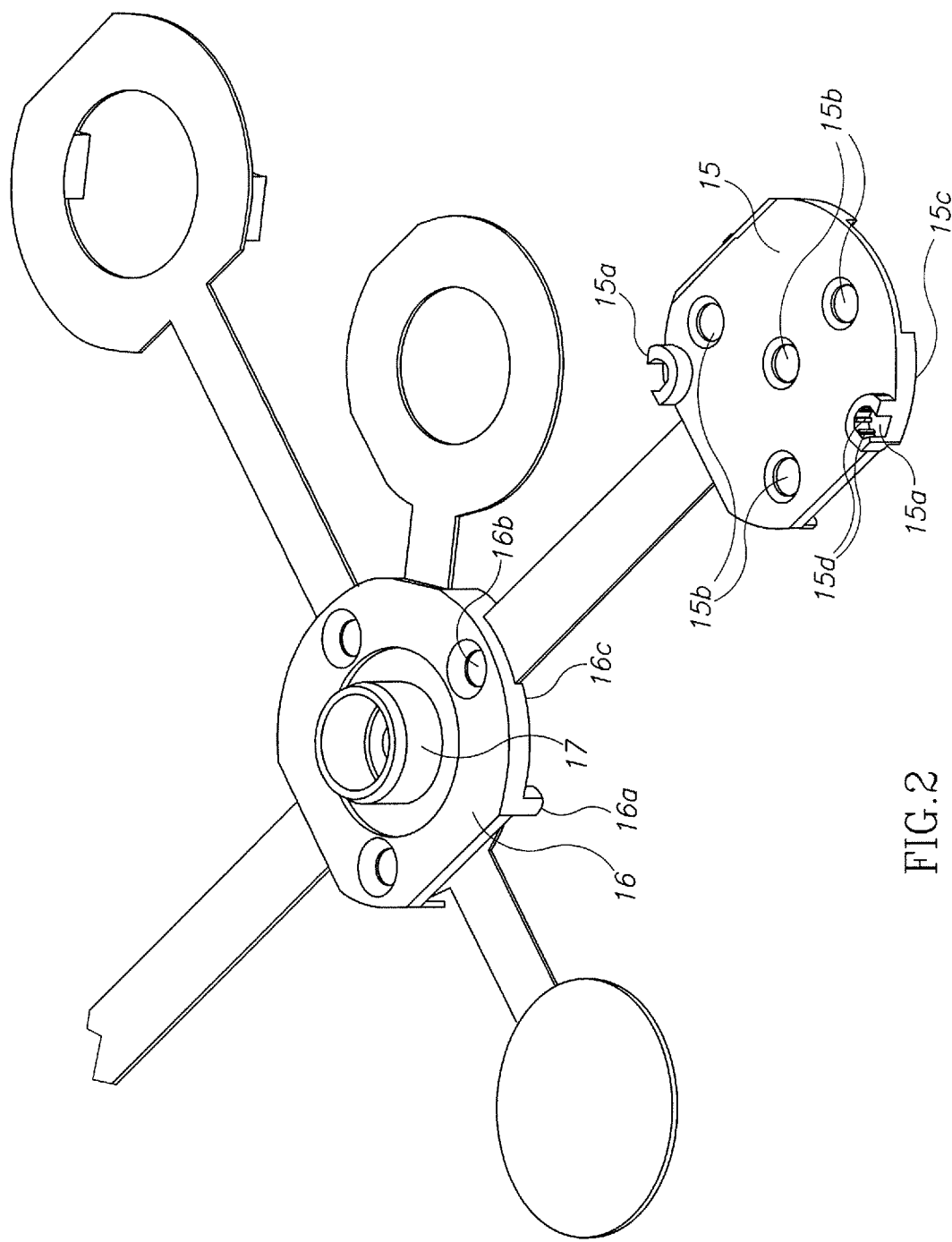
FIG. 2 is a schematic illustration of a bottom view of a portion of a full-flex PCB in accordance with an embodiment of the present invention.

Reference is now made to FIG. 2 which is a schematic illustration of a bottom view of a portion of a full-flex PCB, in accordance with an embodiment of the present invention. In some embodiments, the full-flex PCB 100 has a somewhat solid support or stiffener for supporting some of the flexible installation units. In order for the full-flex PCB 100 to be easily assembled, some of the installation units may have a solid support (e.g., supports or stiffeners 15 and 16), which may be placed on the underside of the flexible installation unit, opposite the electrical components in order to support them. A frill-flex PCB is difficult to fold and maintain in a folded configuration without a solid support placed on the installation units which carry the electrical components thereon. Typically, the flexible installation units which may include a solid support may be those installation units onto which other installation units are folded. As will be described later, flexible installation units 110 capable of having a transmitter disposed thereon, and flexible installation units 11 and 11' capable of having an imager disposed thereon may be considered as the "core" units. Since, according to some embodiments, the remainders of the flexible installation units are folded over these three flexible installation units, these three units 110, 11 and 11' (and no other flexible installation units) are typically supported by a solid support. In other embodiments, additional or other flexible installation units may have a solid support attached on the component's free side.

Furthermore, when the in-vivo sensing device into which full-flex PCB 100 is folded includes a one or more batteries, the solid supports provide an opposing force against the batteries through the battery contacts (installed on flexible installation units 13 and 13'). The batteries should to be tightly held between the battery contacts so as to provide power to all the electrical components installed on the full-flex PCB 100. When the full-flex PCB 100 is folded and inserted into an in-vivo device's housing, the solid supports through the battery contacts may push against the batteries held therebetween. The supports may be made of any thermoplastic polymer such as Acetal, ABS, Polycarbonate, and Polyimide. Other materials may be used.

Figure 3:
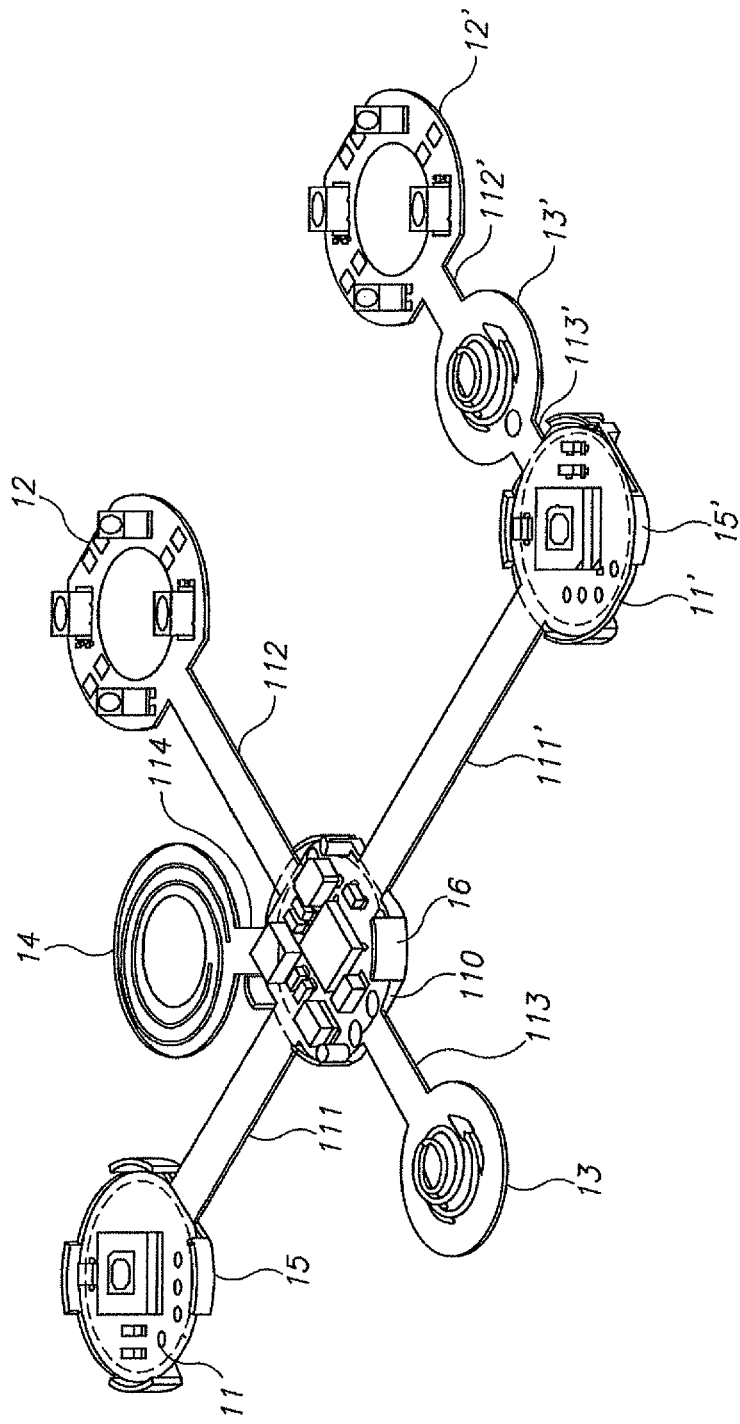
FIG. 3 is a schematic illustration of a top view of a full-flex PCB in an unfolded configuration, in accordance with an embodiment of the present invention.

FIG. 2 illustrates two solid supports 15 and 16. Support 15 may be placed under flexible installation unit 11 (as shown in FIG. 3 from a top view), to prevent installation unit 11 from bending or folding. In some embodiments, there may be another support 15', which is for supporting flexible installation unit 11' (as shown in FIG. 3). In some embodiments, the supports or stiffeners may be designed such that, when full-flex PCB 100 is folded, the supports may be connected to one another so as to assist in maintaining a folded configuration before the PCB is inserted into an in-vivo device's housing. For example, support 15 may include a female element 15*a* essentially constituted by a semi-cylindrical casing. During a full-flex PCB folding process, a male element 16*a* essentially constituted by a cylinder may be press fitted into female element 15*a* in order to maintain a folded configuration to those flexible installation units attached to supports 15 and 16 (as will be shown in FIGS. 7 and 8, flexible installation unit 11 is folded over flexible installation unit 110 and under flexible installation unit 12, and then folded over flexible installation unit 12, followed by press fitting of female element 15*a* into male element 16*a*). In some embodiments, male element 16*a* may be part of support 16, which may be attached to flexible installation unit 110 capable of having a transmitter disposed thereon (also shown in FIG. 3 from a top view). Typically, support 15 may comprise two female elements 15*a*, and support 16 may comprise two corresponding male elements 16*a* (only one shown in FIG. 2, since the second one is behind the support 16).

According to some embodiments, female element 15*a* may include on its internal wall and in the axial direction a plurality of protruding ribs 15*d*. The plurality of ribs 15*d* on the internal wall of female unit 15*a* may provide friction when male unit 16*a* is fitted into it. The ribs 15*d* may enable a tighter fit or tighter connection between male unit 16*a* and female unit 15*a*, since male unit 16*a* is actually pushed against the ribs 16*d* when being fit within female unit 15*a*.

In some embodiments, supports 15 and 16 may comprise more than one hole 15*b* and 16*b*, respectively. Holes 15*b* and 16*b* may serve as holes through which glue is applied in order to attach the flexible installation units to their supports. For example, glue may be applied onto one or more of holes 15*b* in order to securely attach flexible installation unit 11 onto support 15. Typically the glue used is UV curing adhesive due to its rapid curing time and high bond strength, but other types of adhesives may be used. In some embodiments, there is no need to apply glue through every hole 15*b* and 16*b*, but rather one hole might suffice in attaching the flexible installation units to supports 15 and 16. In some embodiments, the extra holes which are not used for applying glue may assist in reducing the weight of the supports 15 and 16, since the holes are an absence of material which results in less weight. This may be an important advantage when implementing the full-flex PCB in an in-vivo swallowable device as described above which should have, for example, a specific gravity of around 1.

In some embodiments, supports 15 and 16 may comprise legs or extensions 15*c* and 16*c* which may be positioned on the periphery of supports 15 and 16. Usually there is more than one leg 15*c* and more than one leg 16*c*. Legs 15*c* and 16*c* may provide extra rigidity to supports 15 and 16, respectively. Without legs/extensions 15*c* and 16*c*, the supports 15 and 16 might bend; however, with these legs, there is less chance for that to happen, such that supports 15 and 16 provide a flat mechanical support for the flexible installation units glued onto them. Furthermore, the legs 15*c* and 16*c* may define the borders or boundaries of supports 15 and 16, respectively. When supports 15 and 16 have legs on their periphery, the flexible installation units attached onto them may be properly held between the boundaries of supports 15 and 16 and may be kept in that position during the gluing process and after.

According to some embodiments, support 16 attached to flexible installation unit 110 capable of having a transmitter disposed thereon may further comprise a hollow cylinder 17. Flexible installation unit 14 (see FIG. 1) which is capable of having an antenna disposed thereon may be placed on hollow cylinder 17. Attaching the antenna onto the end of the cylinder ensures that the antenna is positioned at a distance from the transmitter and from the batteries (as will be shown later during the folding process in FIG. 12) which is important so that the operation of the antenna and the transmitter would not be disrupted or damaged. Other methods of ensuring the position of the antenna at a distance from the transmitter and the batteries may be used.

Reference is now made to FIG. 3 which is a schematic illustration of a top view of a full-flex PCB in an unfolded configuration, in accordance with an embodiment of the present invention. FIG. 3 illustrates the solid supports attached to the flexible installation units from a top view, i.e., opposite the side shown in FIG. 2. According to some embodiments, support 15' is attached to flexible installation unit 11' capable of having a first imager disposed thereon. Support 15 is attached to flexible installation unit 11 capable of having a second imager disposed thereon, and support 16 is attached to flexible installation unit 110 capable of having a transmitter disposed thereon. In some embodiments, as described in FIG. 2 above, supports 15, 15' and 16 may include a plurality of solid legs or extensions on their periphery, which may provide further mechanical support to the flexible installation unit attached and/or glued onto the solid support. These extensions may act as a frame which holds the flexible installation unit in place within the solid support. Typically, the position of one extension in relation to another would be designed so as to provide centralization of the flexible installation unit within the support. For example, if the support comprises four extensions, their position in relation to one another would typically be symmetrical, such that the distance between one extension to another would be the same. Furthermore, these extensions provide stiffness to the support such that the support would maintain its flat structure and ensure mechanical support for the flexible installation unit within.

Figure 4:
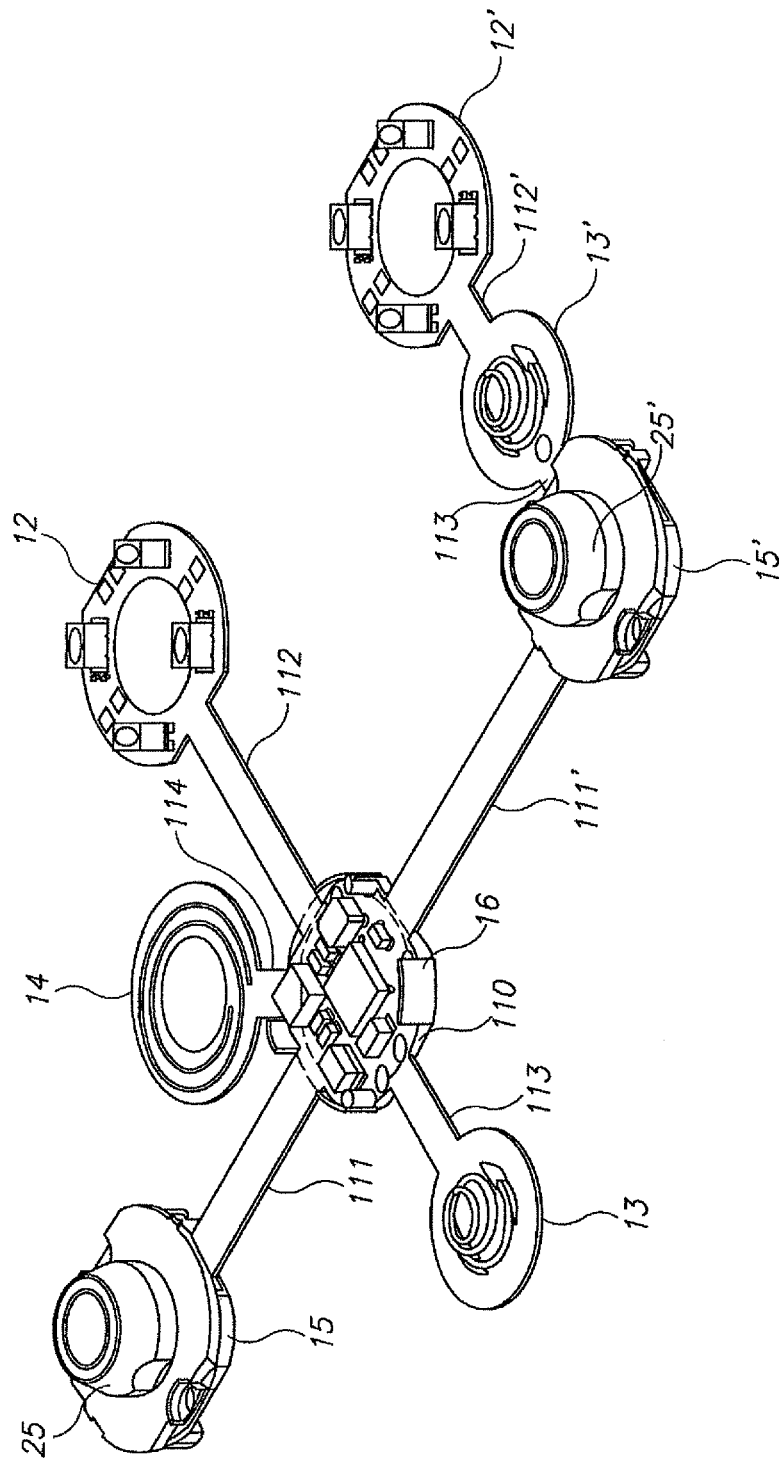
FIG. 4 is a schematic illustration of a top view of a full-flex PCB in an unfolded configuration, in accordance with some embodiments of the present invention.

Reference is now made to FIG. 4 which is a schematic illustration of a top view of a full-flex PCB in an unfolded configuration, in accordance with some embodiments of the present invention. FIG. 4 illustrates two optical assemblies placed onto the flexible installation units capable of having an imager disposed thereon, while covering the imager. In some embodiments, optical assembly 25' may be placed over flexible installation units 11' capable of having a first imager disposed thereon, and optical assembly 25 may be placed onto flexible installation unit 11 capable of having a second imager disposed thereon. According to some embodiments, the optical assembly (25 and/or 25') may comprise mirrors, prisms, composite lenses or any other suitable focusing and/or light directing elements. In some embodiments, the optical assembly (25 and/or 25') may comprise a lens holder and lenses incorporated within the lens holder. The lens holder may be designed to be positioned at a specific location over each imager so as to focus illumination reflected from in-vivo tissue onto the imager (whether it is an imager installed on flexible installation unit 15 or 15'). The optical assembly may have an aperture through which reflected illumination penetrates.

According to some embodiments, a full-flex circuit board width has a tight tolerance. A full-flex PCB has a final width of typically 0.05-0.06 mm, and the tolerance is of about ±5 μm (or 0.005 mm) which is of an order of magnitude smaller than the final width of the full-flex PCB. Furthermore, full-flex PCB has a tight tolerance in the "x-y" axes due to a very accurate layout cutting of the PCB. This may be crucial when assembling optical systems such as optical assemblies 25 and 25'. The tight tolerances described may assist in adjusting the illumination sources in an accurate position along the folded full-flex PCB, e.g., the orientation in space in "x-y" axes of the LED ring installed on flexible installation units 12 and 12' around a lens holder disposed within their corresponding optical assemblies 25 and 25'. The accurate layout cutting of the PCB ensures that the LED ring surrounds the lens holder while conforming to a specific optical layout. Further, the full-flex PCB's tight tolerances may assist in adjusting the position of the imager and the optical system in relation to the optical window (in "x-y-z" axes), so as to avoid the incidence of stray light from the optical window which covers the imaging assembly (shown later as ref numbers 250 and 250').

Figure 5:
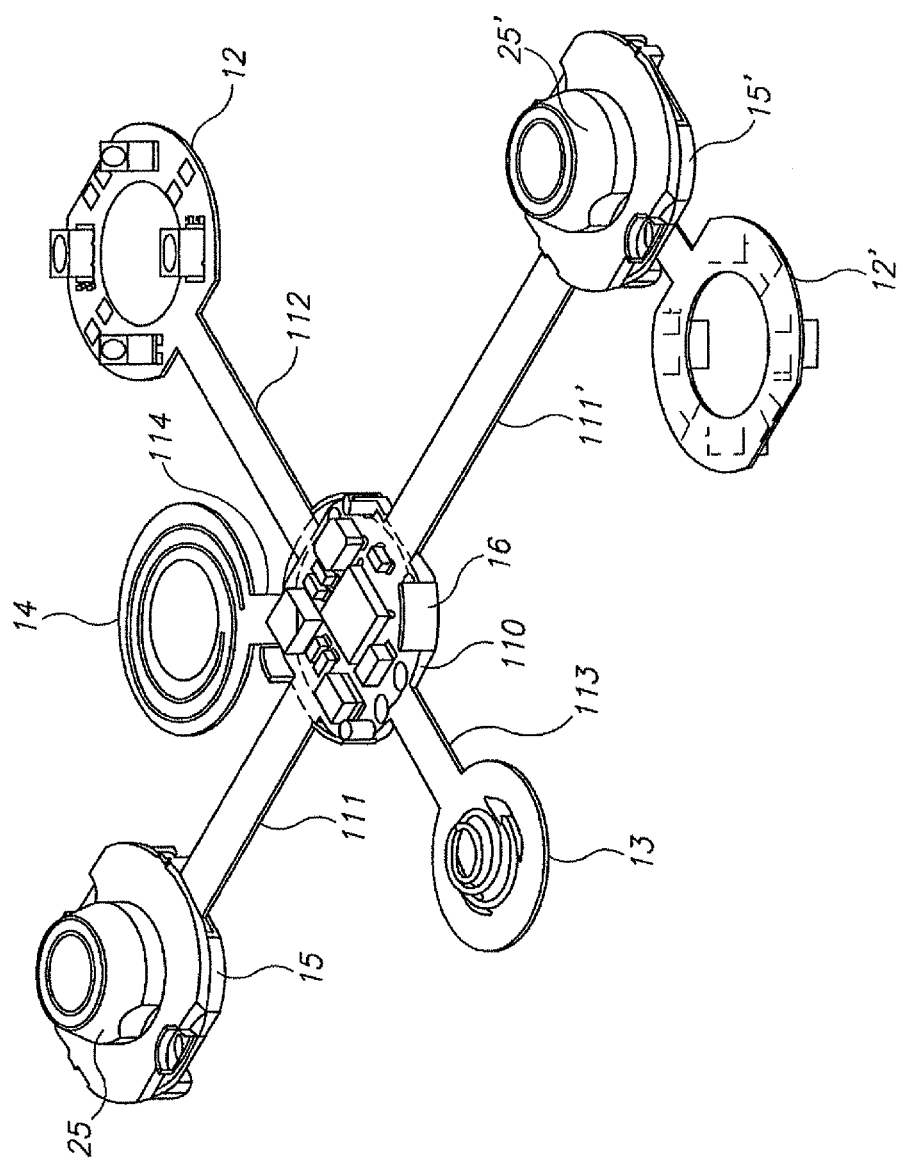
FIGS. 5-12 schematically illustrate a method of folding a full-flex PCB in accordance with some embodiments of the present invention.
Figure 6:
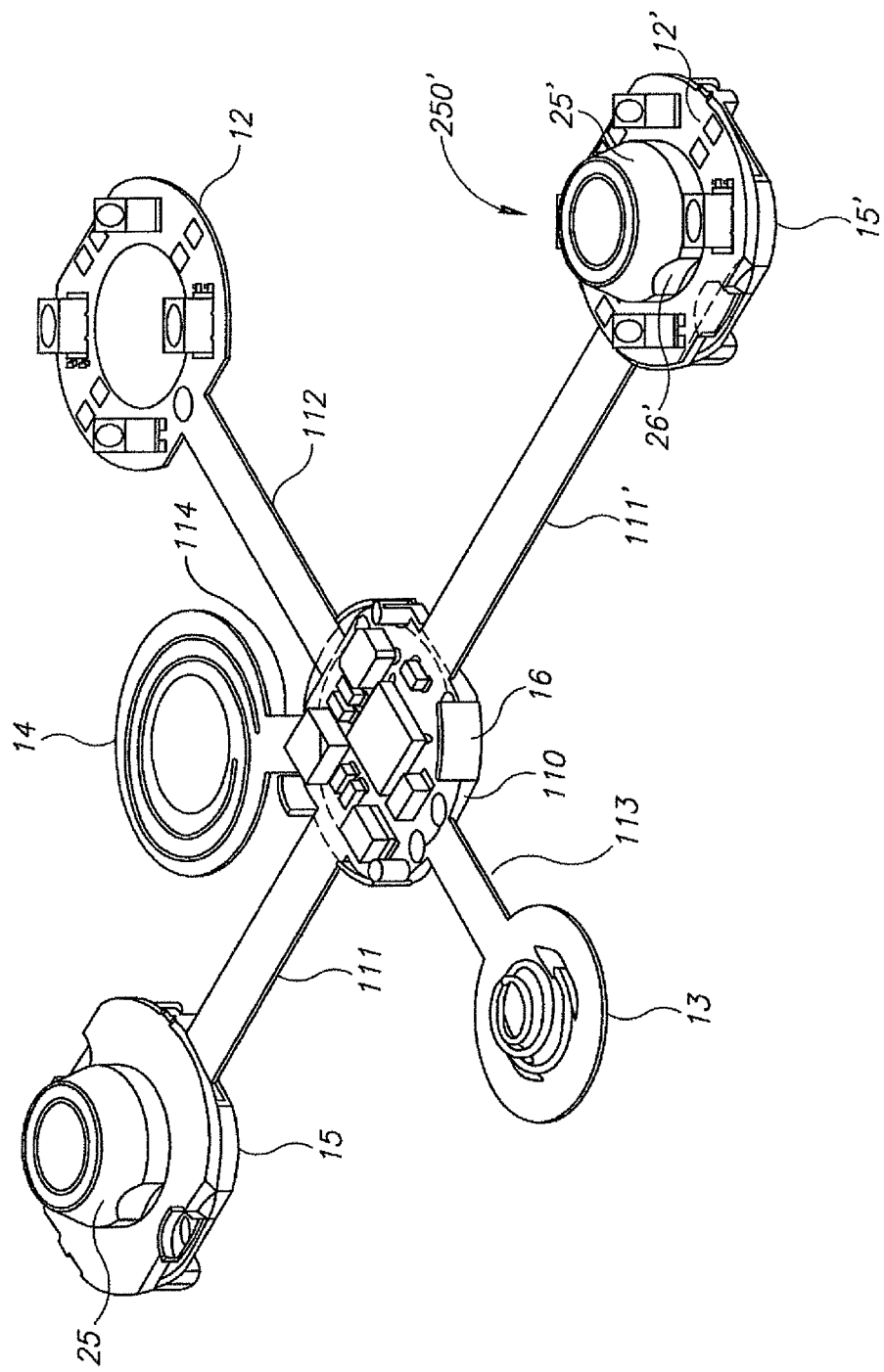

Reference is now made to FIGS. 5-12, which schematically illustrate a method of folding a full-flex PCB, in accordance with some embodiments of the present invention. In FIG. 5, flexible connection unit 113' and flexible installation unit 13' configured to having disposed on a first battery contact, shown in FIG. 4, have been folded beneath flexible installation unit 11', which is capable of having a first imager disposed thereon. This fold may lead to flexible connection unit 112' and flexible installation unit 12' capable of having illumination sources disposed thereon to appear in FIG. 5 as upside down, i.e., the side with no components being up. In FIG. 6, the flexible installation unit 112' has been folded over, such that flexible installation unit 12' is placed over the optical assembly 25'. In some embodiments, optical assembly 25' may comprise at least two indents 26' positioned opposite one another, onto which glue may be applied in order to affix flexible installation unit 12' onto optical assembly 25' so as to maintain a folded configuration. The indents 26' may uncover some of the surface of optical assembly 25' onto which flexible installation unit 12' is placed, and any suitable adhesive may be applied in order to securely attach the two. Typically, UV curing adhesive is used. This may be the final step resulting in flexible installation units 11', 12' and 13' all to be stacked under the first optical assembly 25' along a common longitudinal axis passing substantially through the center of flexible installation units 11', 12', and 13', thereby creating the first imaging assembly 250'.

Figure 7:
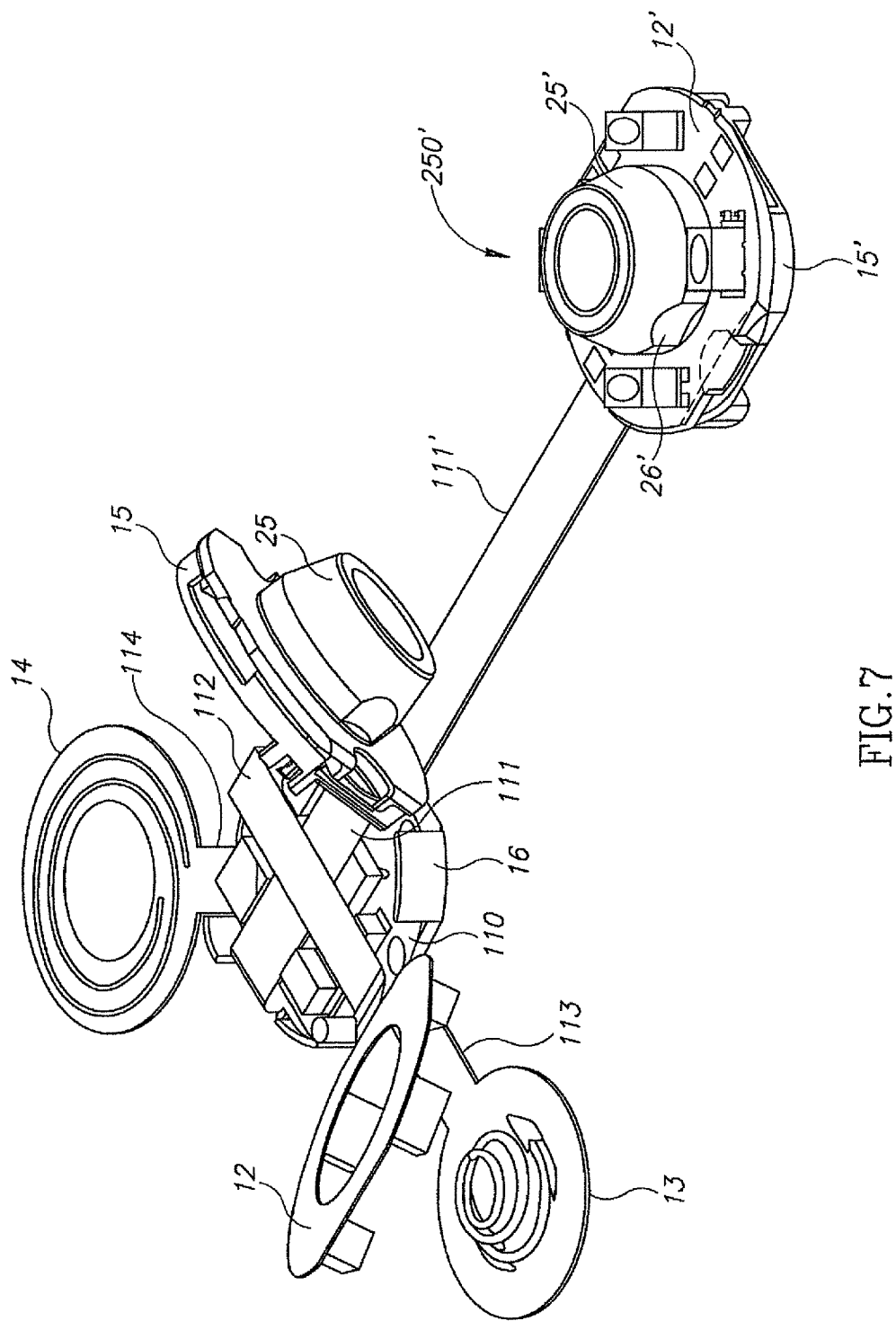

FIG. 7 illustrates another folding step which may take place during assembly process of the full-flex PCB prior to inserting the full-flex PCB into a housing. In FIG. 7, the folding process is taking place over the flexible installation unit 110 capable of having a transmitter disposed thereon. In some embodiments, flexible connection unit 111 may be folded over the flexible installation unit 110 capable of having a transmitter disposed thereon. Subsequently, flexible connection unit 112 may be folded over flexible installation unit 110, such that flexible connection unit 111 and flexible connection unit 112 create a crisscross.

Figure 8:
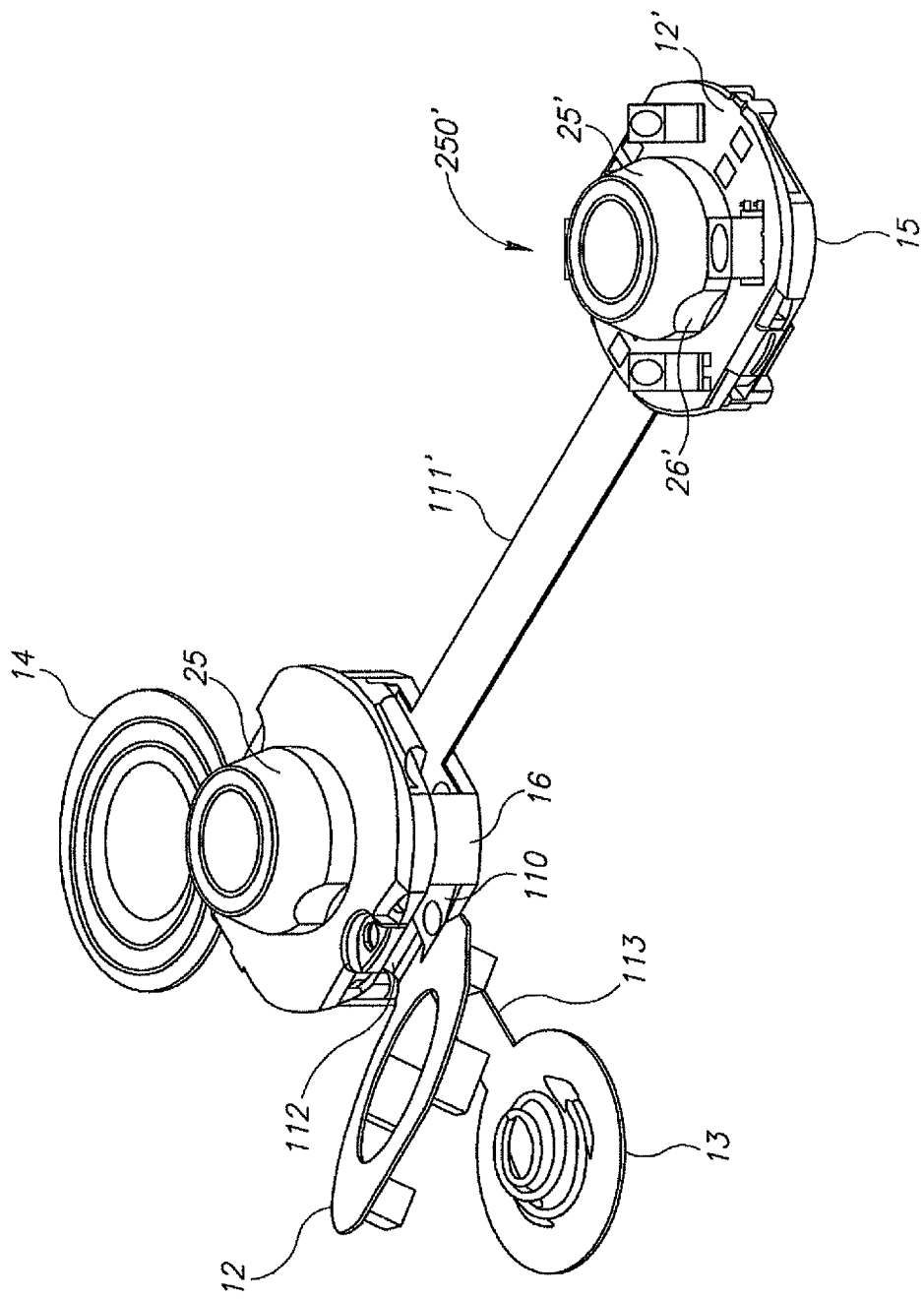
Figure 9:
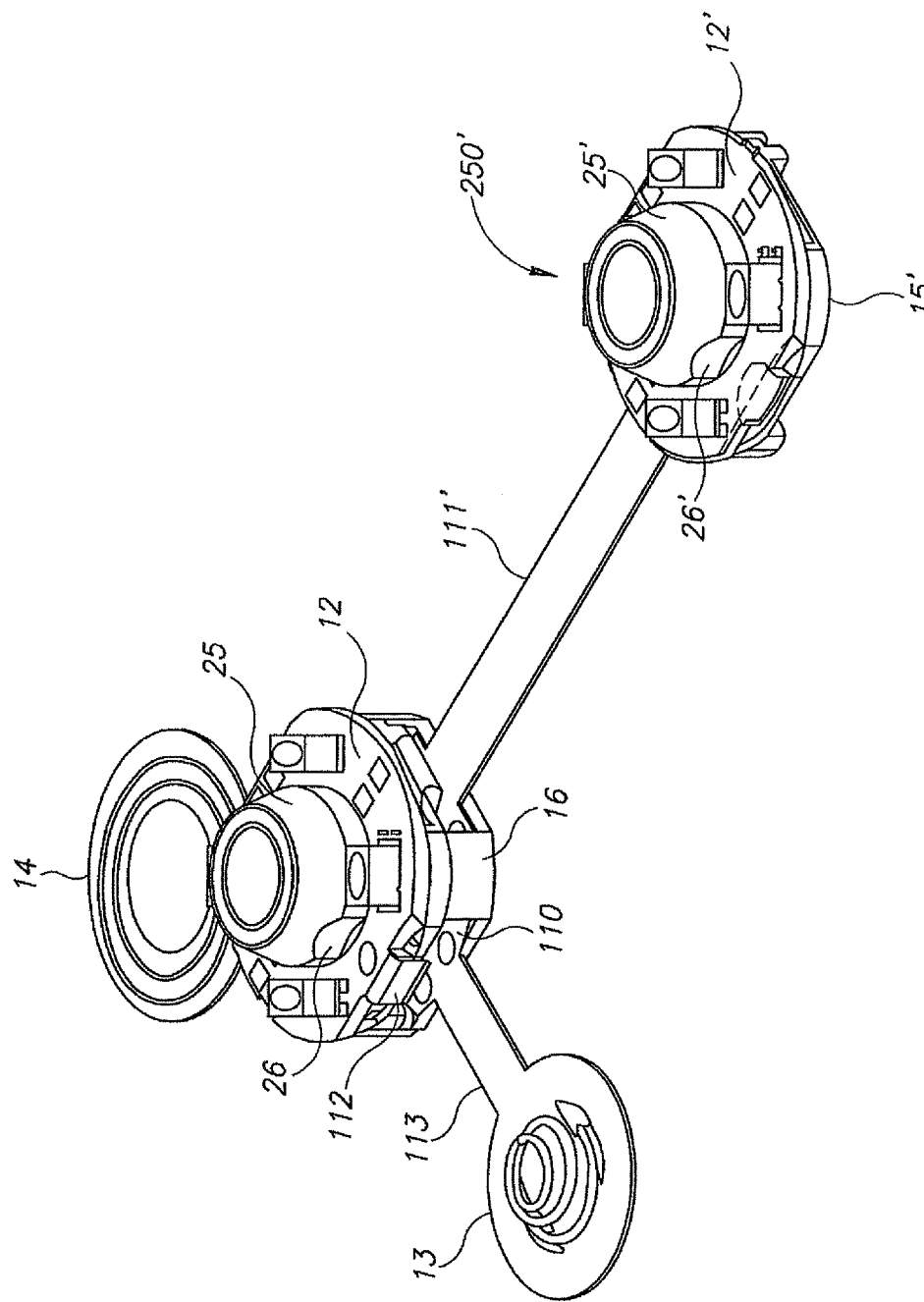

FIG. 8 illustrates the folding of optical assembly 25, which is connected to flexible installation unit 111, over the crisscross, i.e., over folded flexible connection unit 112. In FIG. 9, flexible installation unit 12 capable of having an illumination source disposed thereon is shown as folded over optical assembly 25. In some embodiments, optical assembly 25 may comprise at least two indents 26, positioned opposite one another, onto which glue may applied in order to affix flexible installation unit 12 onto optical assembly 25 so as to maintain a folded configuration. The indents 26 may uncover some of the surface of optical assembly 25 onto which flexible installation unit 12 is placed, and any suitable adhesive may be applied in order to securely attach the two. Typically, UV curing adhesive is applied on the indents 26.

Figure 10:
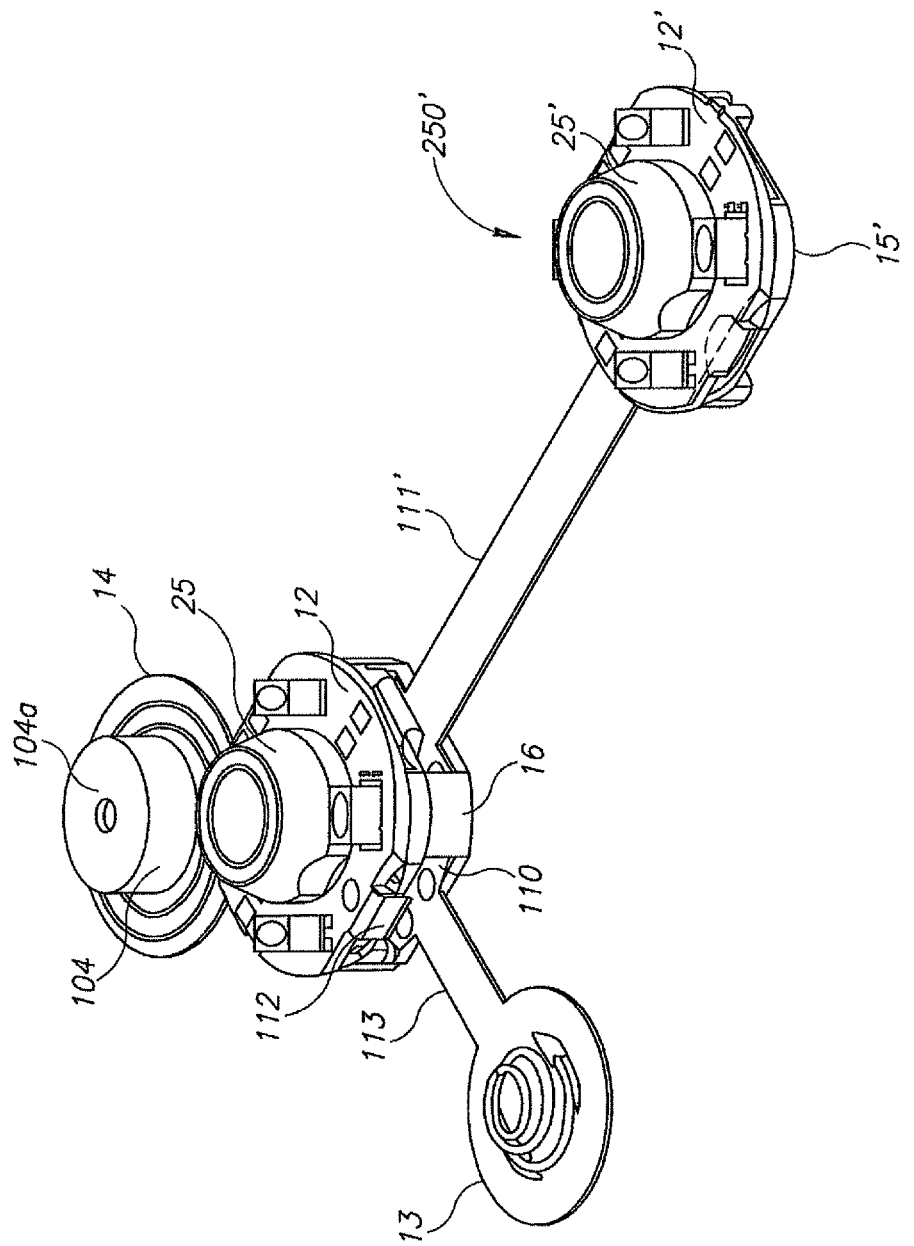

FIG. 10 illustrates a hollow cylinder 104 with a cover 104a having been inserted through the hole in flexible installation unit 14 onto which an antenna is installed.

Figure 11:
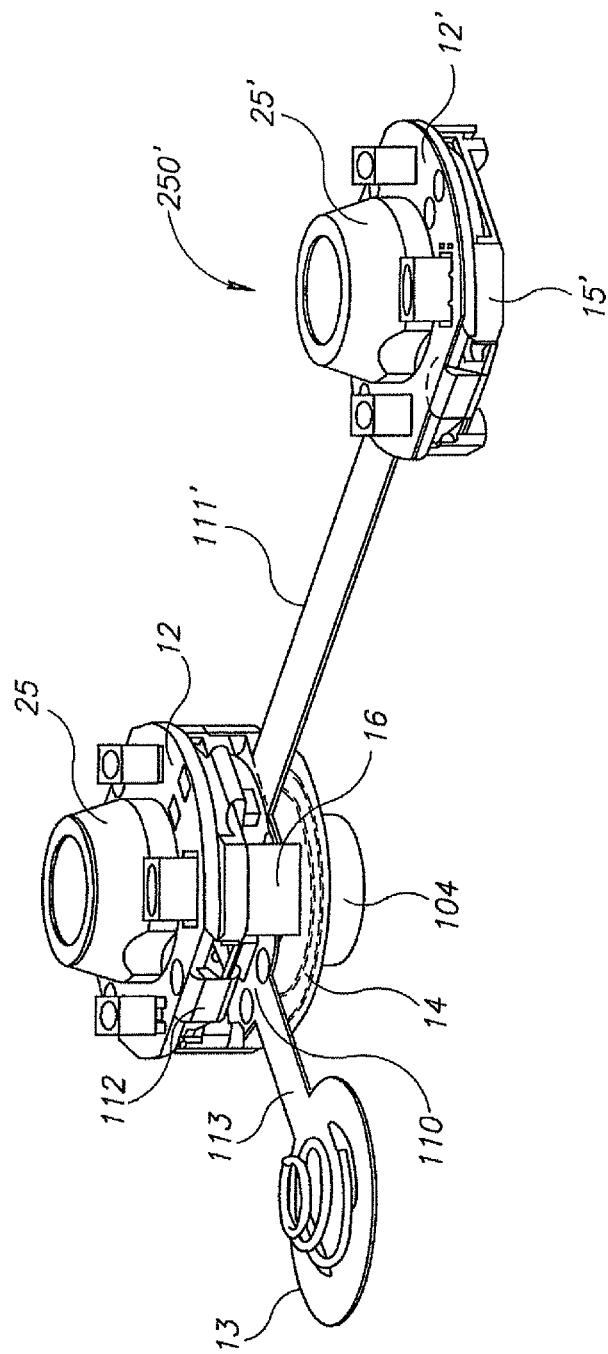

In FIG. 11, flexible connection unit 114 is shown as having been folded under support 16 such that flexible installation unit 14 along with hollow cylinder 104 are folded opposite optical assembly 25. According to some embodiments, cylinder 17 (which is illustrated in FIG. 2) has a smaller diameter than cylinder 104. In some embodiments, hollow cylinder 17 may be inserted into hollow cylinder 104 such that flexible installation unit 14 onto which an antenna is installed may lean on the edge of hollow cylinder 104. In some embodiments, the flexible installation unit 14 may lean on cylinder 104 when the diameter of cylinder 104 is larger than the diameter of cylinder 17, and when the diameter of the opening in flexible installation unit 14 (through which cylinder 17 passes) is smaller than the diameter of cylinder 104. When the flexible installation unit 14 leans on hollow cylinder 104, the antenna installed onto it maintains a distance from the transmitter so that the functionality and efficiency of the antenna would not be disrupted or even damaged.

Figure 12:
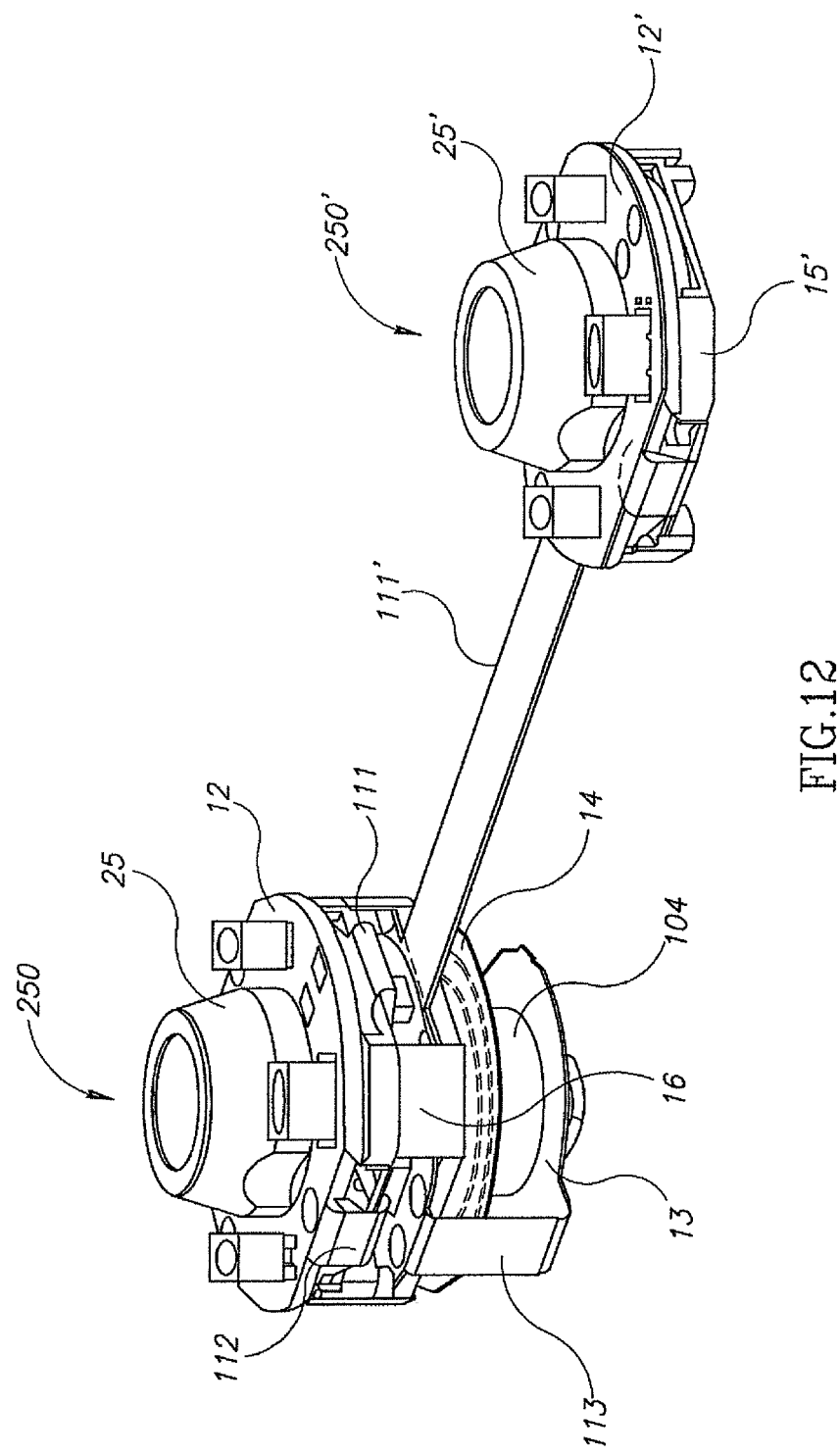

FIG. 12 illustrates the final folding step resulting in a second imaging assembly 250, which is connected by flexible connection unit 111' to a first imaging assembly 250'. In FIG. 12, flexible connection unit 113 may be folded under support 16 such that flexible installation unit 13 capable of having a second battery contact disposed thereon may be folded over cylinder 104. In some embodiments, flexible installation unit 13 may be glued onto cover 104a of cylinder 104, in order to keep the flexible installation unit 13 securely attached to cylinder 104. In some embodiments, flexible installation units 11, 12, 13 and 14 may be stacked under the second optical assembly 25 along a common longitudinal axis passing substantially through the center of flexible installation units 11, 12, 13 and 14, thereby creating the second imaging assembly 250.

It is well known that an antenna should not be too close to metal elements that might cause disruptions or damage to the operation of the antenna. This is why the full-flex PCB is designed so that the antenna is not near the transmitter or the batteries. According to some embodiments, the antenna installed on flexible installation unit 14 may be positioned at a distance from both the transmitter (as described above regarding FIG. 11) and from the second battery contact installed on flexible installation unit 13. As shown in FIG. 11, the antenna may be distant from the transmitter since it leans on the step created by the larger diameter of cylinder 104 compared to cylinder 17. Furthermore, as shown in FIG. 12, the antenna may be distant from the second battery contact installed on flexible installation unit 13, since the second battery contact is attached onto cover 104a which is far from the antenna in at least the height of cylinder 104. The second battery contact being distant from the antenna is equivalent to the batteries being distant from the antenna. The height of cylinder 104 may be designed according to the required distance between the battery and the antenna that would not cause any interruptions to antenna performance, i.e., transmission of in-vivo data to a receiver.

Figure 13:
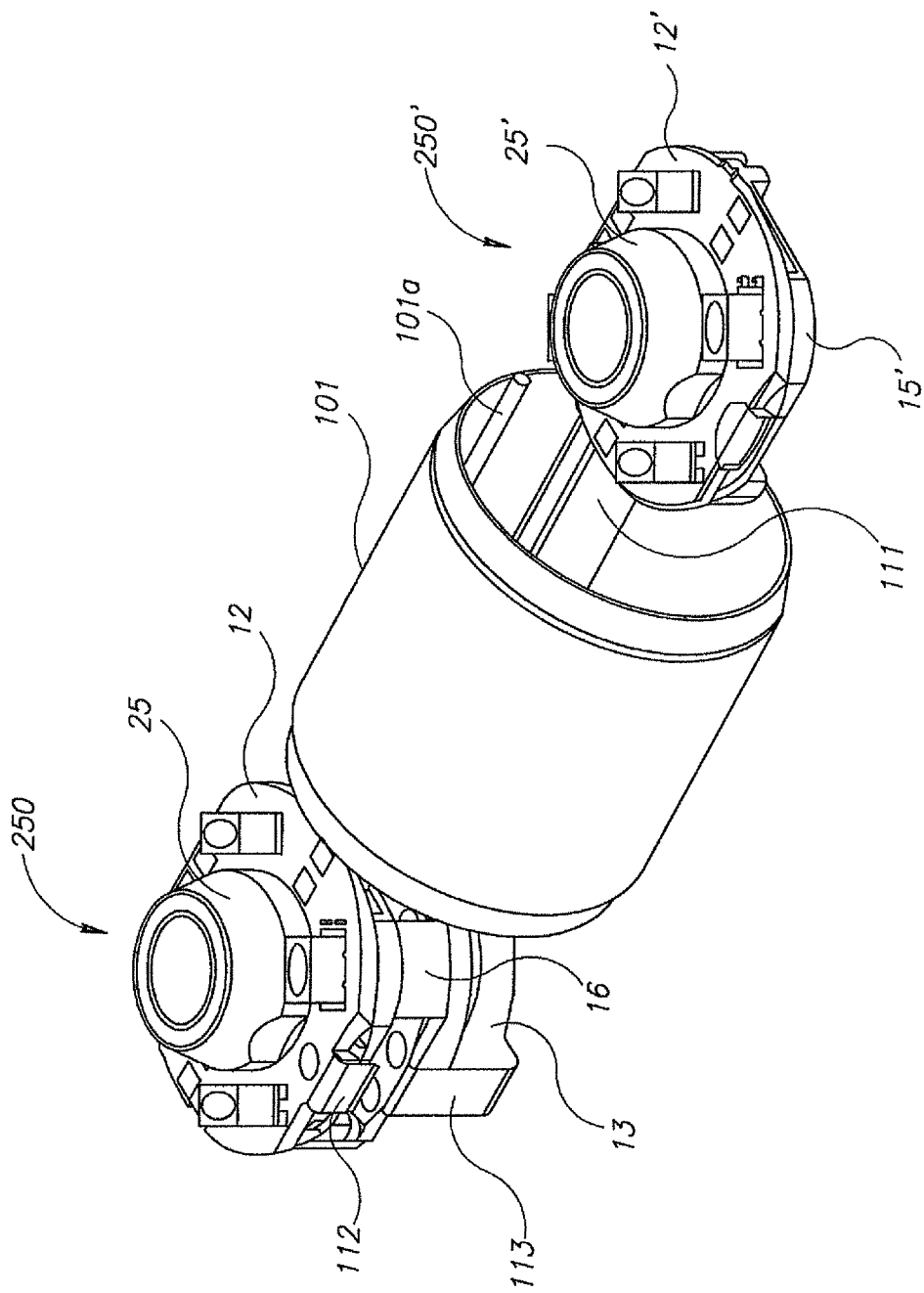
FIGS. 13-15 schematically illustrate a method of assembling an in-vivo imaging device, in accordance with some embodiments of the present invention.
Figure 14:
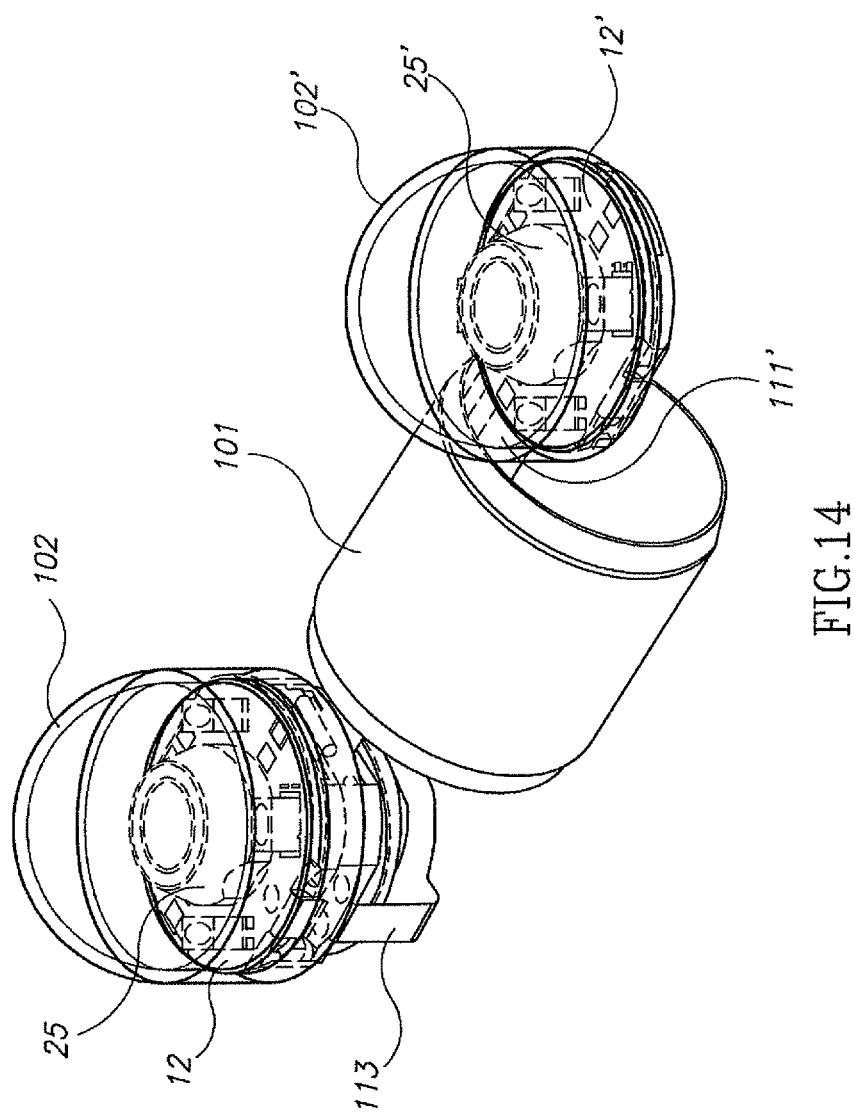
Figure 15:
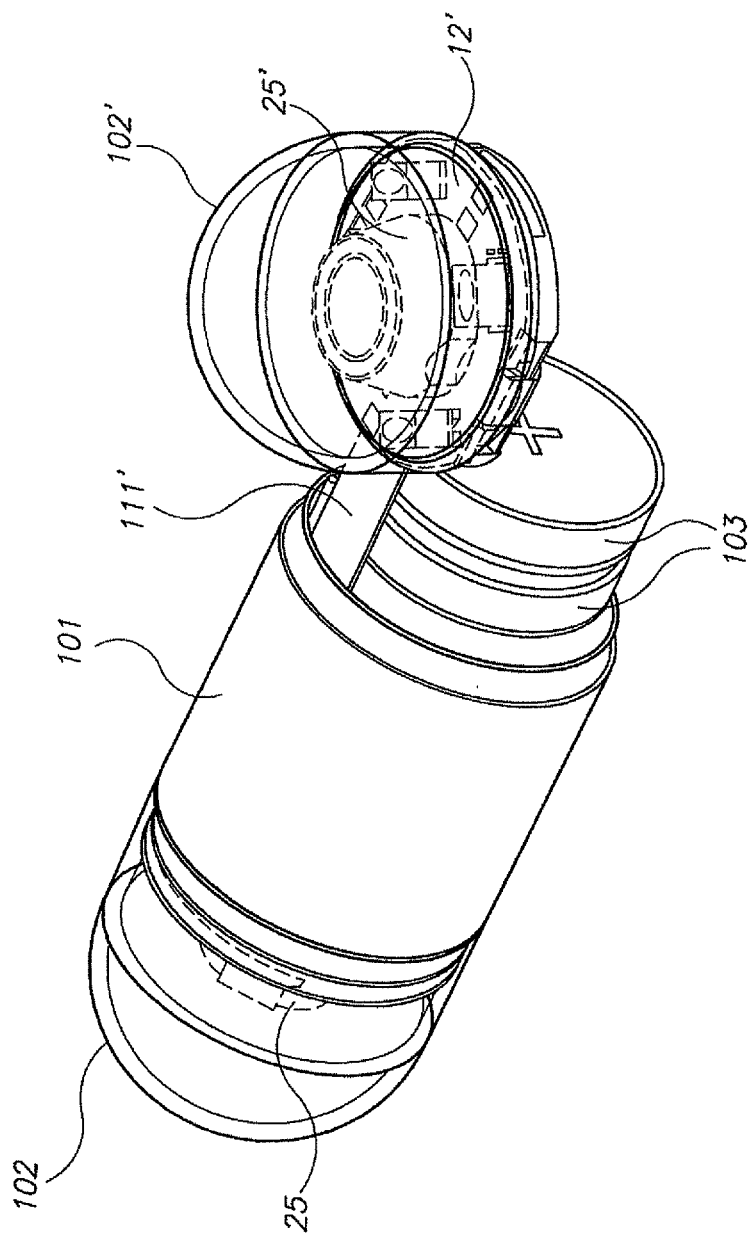

Reference is now made to FIGS. 13-15. FIGS. 13-15 schematically illustrate a method of assembling an in-vivo imaging device, in accordance with some embodiments of the present invention. In FIG. 13, first imaging assembly 250' and thereafter flexible connection unit 111' may be passed through housing 101. In some embodiments, housing 101 may comprise two open ends. In some embodiments, housing 101 may further comprise protruding ribs on its inner wall along the longitudinal axis, such as rib 101a. Rib 101a may assist in guiding flexible connection unit 111' through housing 101. In some embodiments, flexible connection unit 111' may be passed through housing 101 between two ribs, such that the ribs may assist in positioning the flexible connection unit 111' at a certain location along the housing 101. This may further ease the assembly process, by preventing the flexible connection unit from freely moving within the housing 101, such that imaging assemblies 250 and 250' along with the flexible connection unit 111' inserted between the housing's ribs create a some what stable configuration that may be easier to handle.

In FIG. 14 the imaging assemblies 250 and 250' are covered by optical windows (or domes) 102 and 102', respectively. In this step the optical windows 102 and 102' are placed onto imaging assemblies 250 and 250' while considering any optical limitation, e.g., proper angles and distance between each optical window (102 or 102') and the optical assemblies (25 or 25') it covers, angles between the illumination sources and the optical window, etc.

During the assembly of other in-vivo imaging devices, whether comprising two imaging assemblies or one, the optical window is placed over the imaging assembly only after the imaging assembly is secured within the housing. This may cause great difficulty during assembly, since the imaging assembly and the optical window need to be attached at a certain orientation to one another taking any optical limitation into consideration (as mentioned above). And, after the imaging assembly is connected to the housing, there is typically little room for orientation changes between the optical window and the imaging assembly.

However, according to embodiments of this invention, the optical window is first placed over the imaging assembly and any adjustment may easily be made then, and only after the optical window is secured onto the imaging assembly are these two attached to the housing. This may be possible due to the length of flexible connection unit 111'. Since flexible connection unit 111' is longer than the length of housing 101, it may be possible to first attach the optical windows onto the imaging assemblies and only then connect the optical windows to the housing 101.

In FIG. 15, optical window 102 covering second imaging assembly 250 may be securely attached to housing 101. According to some embodiments, optical window 102 is securely attached to housing 101 by glue, laser welding or any other attachment means that provides a tight seal. At least one battery 103 may be inserted into housing 101, which may contact the second battery contact installed on flexible installation unit 13. In some embodiments, flexible connection unit 111' is longer than the length of housing 101, which as described above enables locking of the optical windows 102 and 102' onto the imaging assemblies 250 and 25' prior to attachment of the optical windows into the housing 101. However, only due to the fact that the flexible connection unit 111' is indeed flexible and not rigid and due to its thinness is it possible to fold the extra length inside the housing 101. Since flexible connection unit 111' is flexible and very thin, it may be possible to push the extra length of flexible connection unit 111' inside housing 101 without causing any damage to the circuitry passing through flexible connection unit 111'. The extra length of flexible installation unit's 111 may be pushed into the housing 101 before locking the dome 102' onto housing 101, and since the flexible connection unit 111' is flexible and thin there is enough space for it between the batteries 103 and housing's 101 inner walls. Optical window 102' may be securely attached to housing 101 by glue, laser welding or any other attachment means that provides a tight seal.

Figure 16:
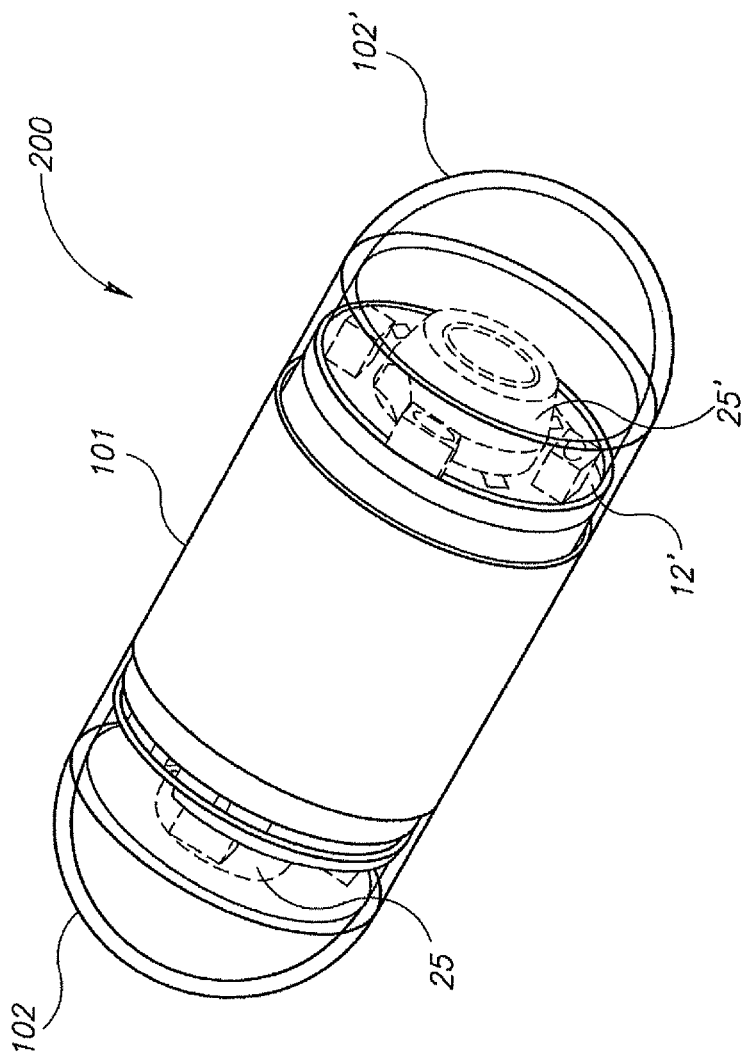
FIG. 16 schematically illustrates a perspective view of the in-vivo imaging device shown in FIG. 15 in an assembled state.

Reference is now made to FIG. 16, which schematically illustrates a perspective view of the in-vivo imaging device shown in FIG. 15 in an assembled state. FIG. 16 illustrates an in-vivo sensing device 200 which is in fact the assembled state of the in-vivo device assembled in FIGS. 12-15. In-vivo sensing device 200 may comprise housing 101 and two domes 102 and 102' covering imaging assemblies 250 and 250', respectively. Housing 101 and domes 102 and 102' may constitute a closed housing which encloses the full-flex PCB described in FIGS. 1-11. Following intake by a patient, either by swallowing, ingestion, or insertion using an endoscope and the like, device 200 may illuminate and acquire images of opposite sides of a lumen within the patient's body, e.g., the GI tract. The in-vivo device 200 may have a wide field of view, e.g., 170 degrees, depending on various optical design preferences, such as the distance between the dome and the optical assembly, the distance between the optical assembly and the imager, etc.

Figure 17:
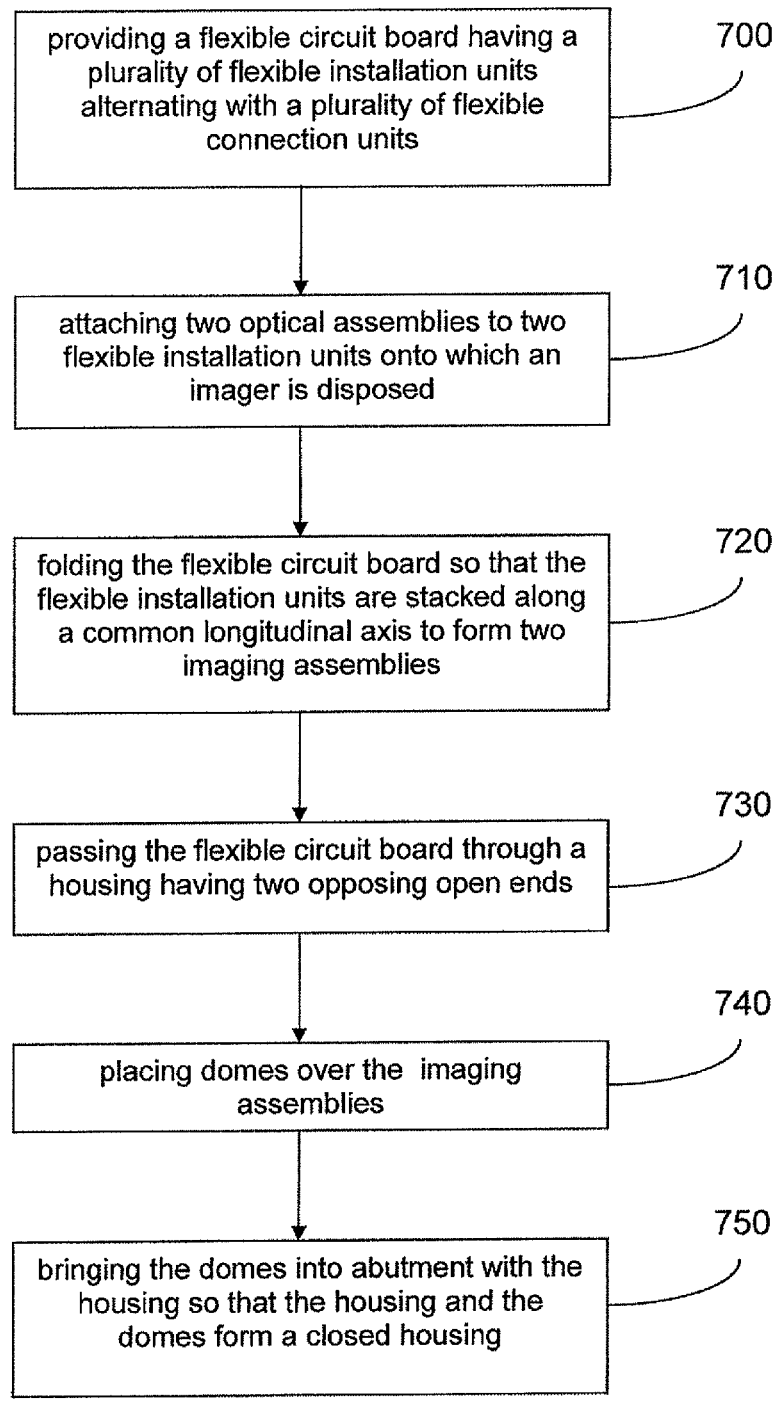
FIG. 17 is a flow-chart illustrating a method of assembling an in-vivo device according to an embodiment of the present invention.

Reference is now made to FIG. 17 which is a flow-chart illustrating a method of assembling an in-vivo imaging device according to an embodiment of the present invention. In step 700, a flexible circuit board is provided. In some embodiments, the flexible circuit board may be full-flex circuit board 100 described above. The full-flex circuit board may comprise a plurality of flexible installation units alternating with a plurality of flexible connection units, such that a flexible connection unit connects between two flexible installation units. In some embodiments, two of the full-flex PCB may be capable of having an imager disposed thereon, e.g., flexible installation units 11 and 11', as shown in FIG. 1, In some embodiments, stiffeners may be attached onto the component-free side of a few flexible installation units. For example, stiffeners 15, 15' and 16 may be attached onto flexible installation units 11, 11' and 110, respectively to provide rigidity prior to folding the PCB (as shown in FIGS. 2 and 3). In step 710, two optical assemblies are attached to two flexible installation units onto which an imager is disposed. One optical assembly is attached over every imager, e.g., optical assembly 25 is attached to flexible installation unit 11, and optical assembly 25' is attached to flexible installation unit 11', as shown in FIG. 4. According to some embodiments, prior to attaching the two optical assemblies to their corresponding flexible installation units, there may be a step of assembling supports or stiffeners onto the PCB, on the component-free side. For example, as shown in FIGS. 2-3, supports 15, 15' and 16 may be glued onto flexible installation units 11, 11' and 110, respectively, in order to provide some rigidity to the flexible PCB 100, thereby enabling easier handling and folding.

In step 720, the flexible circuit board may be folded so that the flexible installation units may be stacked along a common longitudinal axis passing substantially through the center of the flexible installation units, to form two imaging assemblies. As shown in FIG. 12, the flexible installation units are stacked along a common longitudinal axis and under the optical assemblies 25 and 25' to form two imaging assemblies 250 and 250'. Subsequent to folding the full-flex PCB in order to create two imaging assemblies is step 730, which comprises passing the flexible circuit board through a housing. The housing may comprise two opposing open ends, such that when the full-flex PCB is passed through it, a first imaging assembly extends out of one open end of the housing, while the second imaging assembly extends out of the opposite open end of the housing. For example, first imaging assembly 250' protrudes out of one open end of housing 101, while the second imaging assembly 250 protrudes out of the other open side of housing 101, as shown in FIG. 13.

In some embodiments, step 740 may comprise placing optical windows/domes over the two imaging assemblies. While placing the domes over the imaging assemblies, the imaging assemblies are oriented in relation to the domes, such that all optical considerations and requirements are met. For example, as shown in FIG. 14, dome 102 may be placed over imaging assembly 250, while dome 102' may be placed over imaging assembly 250'.

The method may comprise a step of folding the flexible circuit board so that each one of the domes is positioned over a respective open end of the housing. This may be a preceding step to step 750. Step 750 may comprise bringing the domes into abutment with the housing so that the housing and the domes form a closed housing. In some embodiments, the domes are securely attached to the housing after they are firmly attached over their corresponding imaging assemblies. Once the domes are securely attached to the housing, they form a closed housing which encloses the full-flex circuit board. Methods of securely attaching the domes to the housing may include gluing, laser welding or any other method that provides a tight seal.

The domes and the housing may form the closed housing of an in-vivo device, such as in-vivo device 200 (as shown in FIG. 16) which may be inserted into a patient's body lumen, e.g. into the GI tract, acquire in-vivo data and transmit it to means for presenting the sensed data of a body lumen to a user. In some embodiments, the in-vivo data may be image data, pH data, pressure data, temperature data, etc. all depending on the type of sensor attached to the full-flex PCB 100 enclosed within the in-vivo device. In some embodiments, there may be more than one type of sensors attached to the full-flex PCB. According to some embodiments, when the in-vivo device comprises an internal power source, such as batteries, the method may comprise an additional step. The method may comprise the step of inserting a battery into the housing prior to the step of folding the flexible circuit board such that a first dome is placed over a first open end of the housing, and a second dome is placed over a second open end of the housing. The method of inserting a battery should take place prior to the step of bringing the domes into abutment with the housing, such that the one or more batteries may be placed within the housing in order to supply power to the device, and only then the domes may be securely attached to the housing to form a closed housing.

In some embodiments, the method of assembling an in-vivo imaging device may comprise other steps. In some embodiments, the full-flex PCB may be folded to form two imaging assemblies and the two imaging assemblies may be passed along a housing having two open ends. Subsequently, the method may comprise the step of covering each of the two imaging assemblies with a respective dome. The method may comprise the steps of bringing a first dome into abutment with a first open end of the housing, inserting a battery or batteries into the housing (that is now closed from its first end), and bringing the second dome into abutment with the second open end of the housing, in order to form a closed housing of an in-vivo imaging device.

It will be appreciated that the present invention is not limited to what has been particularly shown and described hereinabove. Rather the scope of the present invention is defined only by the claims which follow.

The invention claimed is:

1. A flexible circuit board having a component side and a second side, said flexible circuit board comprising of:
a first flexible installation unit having a first side on which a first imager is disposed;
a second flexible installation unit having a first side on which a second imager is disposed; and
a third flexible installation unit having a first side on which a transmitter is disposed, wherein said third flexible installation unit is connected to each one of the first installation unit and the second installation unit by a flexible connection unit, and wherein said third flexible installation unit is further connected by respective flexible connection units to:
- a fourth flexible installation unit having disposed thereon a first illumination source;
- a fifth flexible installation unit having disposed thereon a first battery contact; and
- a sixth flexible installation unit having disposed thereon an antenna;

and wherein said second flexible installation unit is further connected by a flexible connection unit to a seventh flexible installation unit having disposed thereon a second battery contact, and wherein said seventh flexible installation unit is further connected by a flexible connection unit to an eighth flexible installation unit having disposed thereon a second illumination source.

2. The flexible circuit board according to claim 1, wherein the flexible connection units are foldable so that the second flexible installation unit, the seventh flexible installation unit, and the eight flexible installation unit are stacked along a common longitudinal axis.

3. The flexible circuit board according to claim 1, wherein the flexible connection units are foldable so that the third flexible installation unit and the flexible installation units connected to the third flexible installation unit, except the second flexible installation unit, are stacked along a common longitudinal axis passing substantially through the center of said flexible installation units.

4. The flexible circuit board according to claim 1, wherein the fourth and eight flexible installation units having disposed thereon the first and second illumination sources, respectively, are ring shaped.

5. The flexible circuit board according to claim 1, wherein each of the first and second installation units having disposed thereon the first imager and the second imager, respectively, have attached thereon a support on a second side thereof opposite to the side on which the respective imager is disposed.

6. The flexible circuit board according to claim 1, wherein the third flexible installation unit has attached thereon a support on a second side thereof opposite to the side on which the transmitter is disposed.

7. The flexible circuit board according to claim 1, wherein each flexible installation unit has disposed thereon a component on a first side thereof, wherein the first side of each of the flexible installation units faces the same direction when said flexible circuit board is in an unfolded configuration.

8. The flexible circuit board according to claim 1, wherein an optical assembly is attached to the first side of each of the first and the second flexible installation units onto which the respective imager is disposed.

9. The flexible circuit board according to claim 8, wherein the flexible circuit board is foldable so that the flexible installation units are stacked along a common longitudinal axis to form two imaging assemblies facing in opposite directions.

10. An in-vivo imaging device comprising:
(i) a flexible circuit board comprising,
  a flexible circuit board having a component side and a second side, said flexible circuit board comprising:
   a first flexible installation unit having a first side on which a first imager is disposed;
   a second flexible installation unit having a first side on which a second imager is disposed; and
   a third flexible installation unit having a first side on which a transmitter is disposed, wherein said third flexible installation unit is connected to each one of the first installation unit and the second installation unit by a flexible connection unit, and wherein said third flexible installation unit is further connected by respective flexible connection units to:
   - a fourth flexible installation unit having disposed thereon a first illumination source;
   - a fifth flexible installation unit having disposed thereon a first battery contact; and
   - a sixth flexible installation unit having disposed thereon an antenna;

and wherein said second flexible installation unit is further connected by a flexible connection unit to a seventh flexible installation unit having disposed thereon a second battery contact, and wherein said seventh flexible installation unit is further connected by a flexible connection unit to an eighth flexible installation unit having disposed thereon a second illumination source, and wherein the flexible circuit board is foldable so that the flexible installation units are stacked along a common longitudinal axis to form two imaging assemblies facing in opposite directions;
(ii) a housing, said housing having two opposing open ends; and
(iii) a dome for each imaging assembly, to orient the imaging assembly in relation to the dome, each dome attachable to the housing to form a closed housing for enclosing the imaging assemblies and the flexible circuit board,
wherein the flexible circuit board is foldable so that each one of the domes is positioned over a respective open end of the housing.

11. The in-vivo imaging device according to claim 10, wherein the flexible connection units are foldable so that the second flexible installation unit, the seventh flexible installation unit, and the eight flexible installation unit are stacked along a common longitudinal axis.

12. The in-vivo imaging device according to claim 10, wherein the flexible connection units are foldable so that the third flexible installation unit and the flexible installation units connected to the third flexible installation unit, except the second flexible installation unit, are stacked along a common longitudinal axis passing substantially through the center of said flexible installation units.

13. The in-vivo imaging device according to claim 10, wherein the fourth and eight flexible installation units having disposed thereon the first and second illumination sources, respectively, are ring shaped.

14. The in-vivo imaging device according to claim 10, wherein each of the first and second installation units having disposed thereon the first imager and the second imager, respectively, have attached thereon a support on a second side thereof opposite to the side on which the respective imager is disposed.

15. The in-vivo imaging device according to claim 10, wherein the third flexible installation unit has attached thereon a support on a second side thereof opposite to the side on which the transmitter is disposed.

16. The in-vivo imaging device according to claim 10, wherein each flexible installation unit has disposed thereon a component on a first side thereof, wherein the first side of each of the flexible installation units faces the same direction when said flexible circuit board is in an unfolded configuration.

17. The in-vivo imaging device according to claim 10, wherein an optical assembly is attached to the first side of each of the first and the second flexible installation units onto which the respective imager is disposed.

* * * * *